US012580063B2

(12) United States Patent
Laaksonen et al.

(10) Patent No.: US 12,580,063 B2
(45) Date of Patent: Mar. 17, 2026

(54) METHODS AND SYSTEMS FOR RADIOTHERAPY TREATMENT PLANNING BASED ON DEEP TRANSFER LEARNING

(71) Applicant: SIEMENS HEALTHINEERS INTERNATIONAL AG, Palo Alto, CA (US)

(72) Inventors: Hannu Mikael Laaksonen, Espoo (FI); Sami Petri Perttu, Helsinki (FI); Tomi Ruokola, Espoo (FI); Jan Schreier, Helsinki (FI); Janne Nord, Espoo (FI)

(73) Assignee: SIEMENS HEALTHINEERS INTERNATIONAL AG (CH)

( * ) Notice: Subject to any disclaimer, the term of this patent is extended or adjusted under 35 U.S.C. 154(b) by 796 days.

(21) Appl. No.: 17/414,937

(22) PCT Filed: May 30, 2019

(86) PCT No.: PCT/EP2019/064145
§ 371 (c)(1),
(2) Date: Jun. 16, 2021

(87) PCT Pub. No.: WO2020/126122
PCT Pub. Date: Jun. 25, 2020

(65) Prior Publication Data
US 2022/0051781 A1 Feb. 17, 2022

Related U.S. Application Data

(60) Provisional application No. 62/783,217, filed on Dec. 21, 2018.

(51) Int. Cl.
| | |
|---|---|
| *G16H 20/40* | (2018.01) |
| *A61N 5/10* | (2006.01) |
| *G06N 3/08* | (2023.01) |

(52) U.S. Cl.
CPC ............. *G16H 20/40* (2018.01); *A61N 5/103* (2013.01); *G06N 3/08* (2013.01)

(58) Field of Classification Search
CPC ........ G16H 20/40; G16H 30/40; A61N 5/103; G06N 3/08
See application file for complete search history.

(56) References Cited

U.S. PATENT DOCUMENTS

| | | | |
|---|---|---|---|
| 2017/0360404 A1 | 12/2017 | Gafner et al. | |
| 2018/0052962 A1 * | 2/2018 | Van Der Koijk | ...... G16H 70/20 |

(Continued)

FOREIGN PATENT DOCUMENTS

| | | | |
|---|---|---|---|
| CN | 101505652 A | 8/2009 | |
| CN | 107731298 A | 2/2018 | |
| WO | WO-2018048507 A1 * | 3/2018 | ........... G06T 11/008 |

OTHER PUBLICATIONS

International Search Report and Written Opinion of the International Searching Authority, International application No. PCT/EP2019/064145, Aug. 28, 2019.

(Continued)

*Primary Examiner* — Robert W Morgan
*Assistant Examiner* — Liza Tony Kanaan
(74) *Attorney, Agent, or Firm* — SU IP CONSULTING

(57) ABSTRACT

Example methods and systems for deep transfer learning for radiotherapy treatment planning are provided. One example method may comprise: obtaining (310) a base deep learning engine that is pre-trained to perform a base radiotherapy treatment planning task; and based on the base deep learning engine, generating a target deep learning engine to perform a target radiotherapy treatment planning task. The target deep learning engine may be generated by configuring (330) a variable base layer among multiple base layers of the base deep learning engine, and generating (340) one of multiple target layers of the target deep learning engine by modifying (Continued)

the variable base layer. Alternatively or additionally, the target deep learning engine may be generated by configuring (350) an invariable base layer among the multiple base layers, and generating (360) one of multiple target layers of the target deep learning engine based on feature data generated using the invariable base layer.

22 Claims, 16 Drawing Sheets

(56) References Cited

U.S. PATENT DOCUMENTS

| | | | | |
|---|---|---|---|---|
| 2018/0315188 | A1 * | 11/2018 | Tegzes | .................... G06T 7/11 |
| 2020/0065940 | A1 * | 2/2020 | Tang | .................... G06F 18/214 |

OTHER PUBLICATIONS

Xin Zhen et al., "Deep Convolutional Neural Network with Transfer Learning for Rectum Toxicity Prediction in Cervical Cancer Radiotherapy: A Feasibility Study", Physics in Medicine & Biology, Institute of Physics Publishing, Oct. 11, 2017, pp. 8246-8263, vol. 62, No. 21.

Will Koehrsen, "Transfer Learning with Convolutional Neural Networks in PyTorch", Retrieved on Aug. 16, 2019 from the Internet at <URL: https://towardsdatascience.com/transfer-learning-with-convolutional-neural-networks-in-bytorch-dd09190245ce>, Nov. 26, 2018.

Roland Becker, "Transfer Learning-So können neuronale Netze voneinander lernen", Retrieved on Aug. 16, 2019 from the internet at <URL: https://jaai.de/transfer-learning-1739/>, Feb. 12, 2018.

Jason Brownlee, "A Gentle Introduction to Transfer Learning for Deep Learning", Deep Learning for Computer Vision, Dec. 20, 2017, Retrieved on Aug. 16, 2019 from the Internet at <URL: https://machinelearningmastery.com/transfer-learning-for-deep-learning/>.

* cited by examiner

100

PRE-TRAINING PHASE 201
200
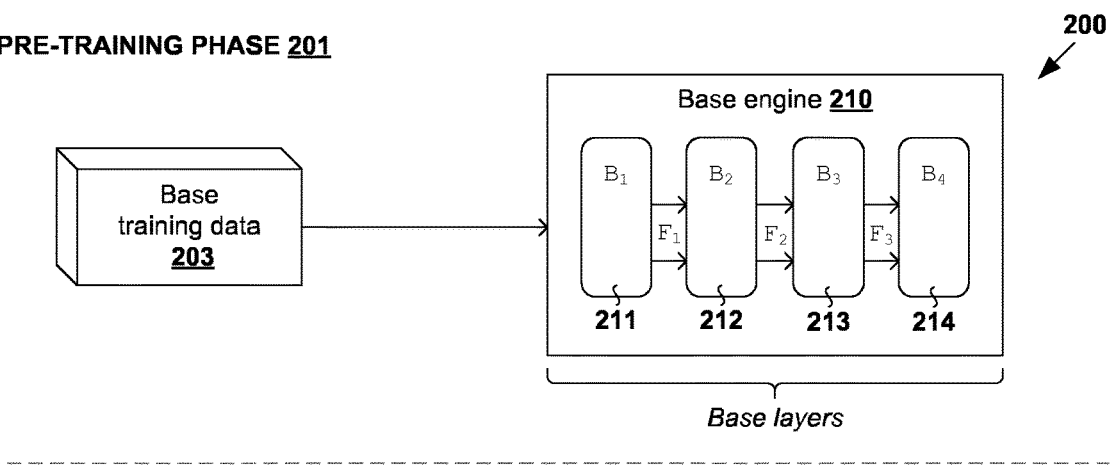
Base layers
---
TRAINING PHASE 202
*Modification 250*
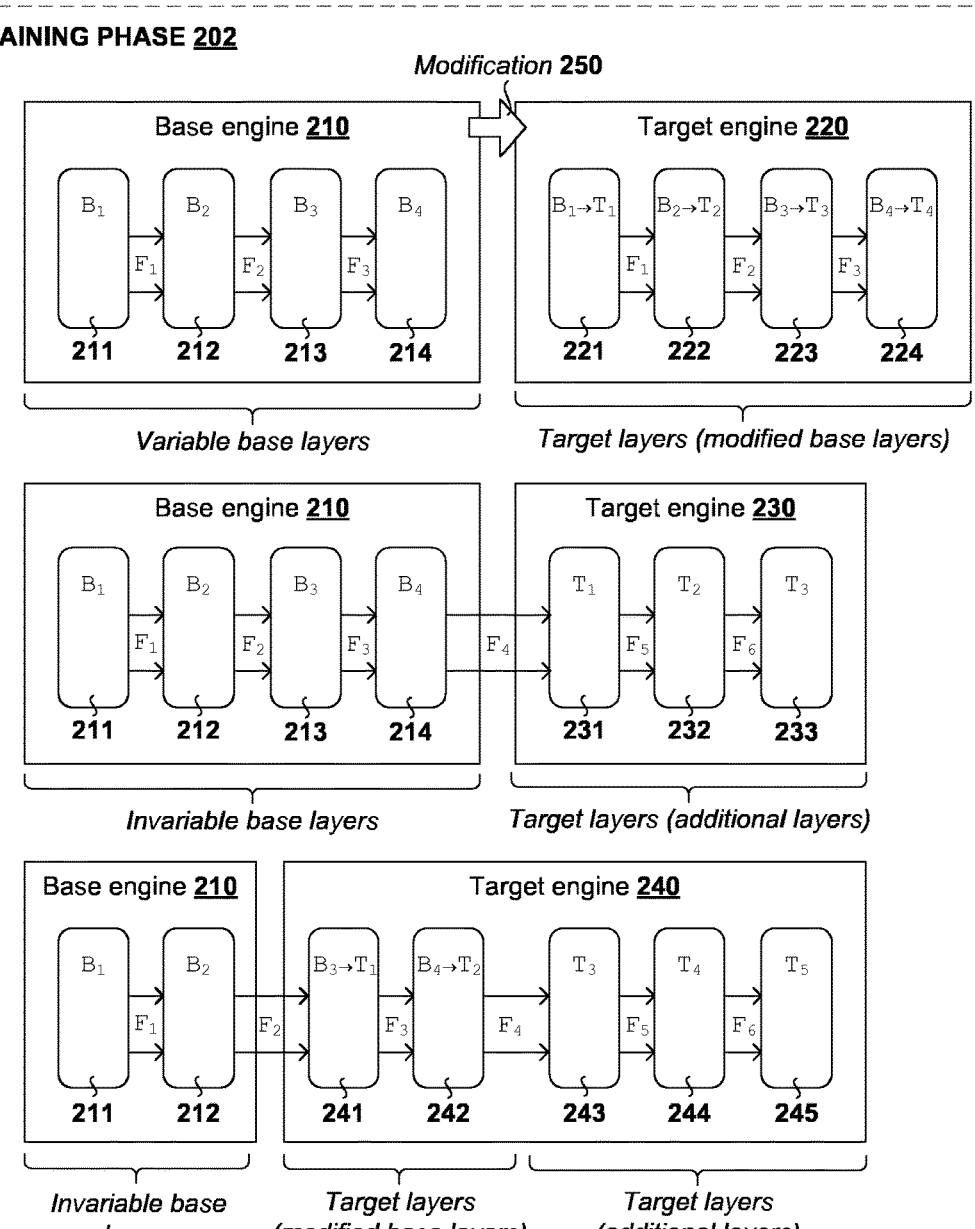
FIG. 2

300

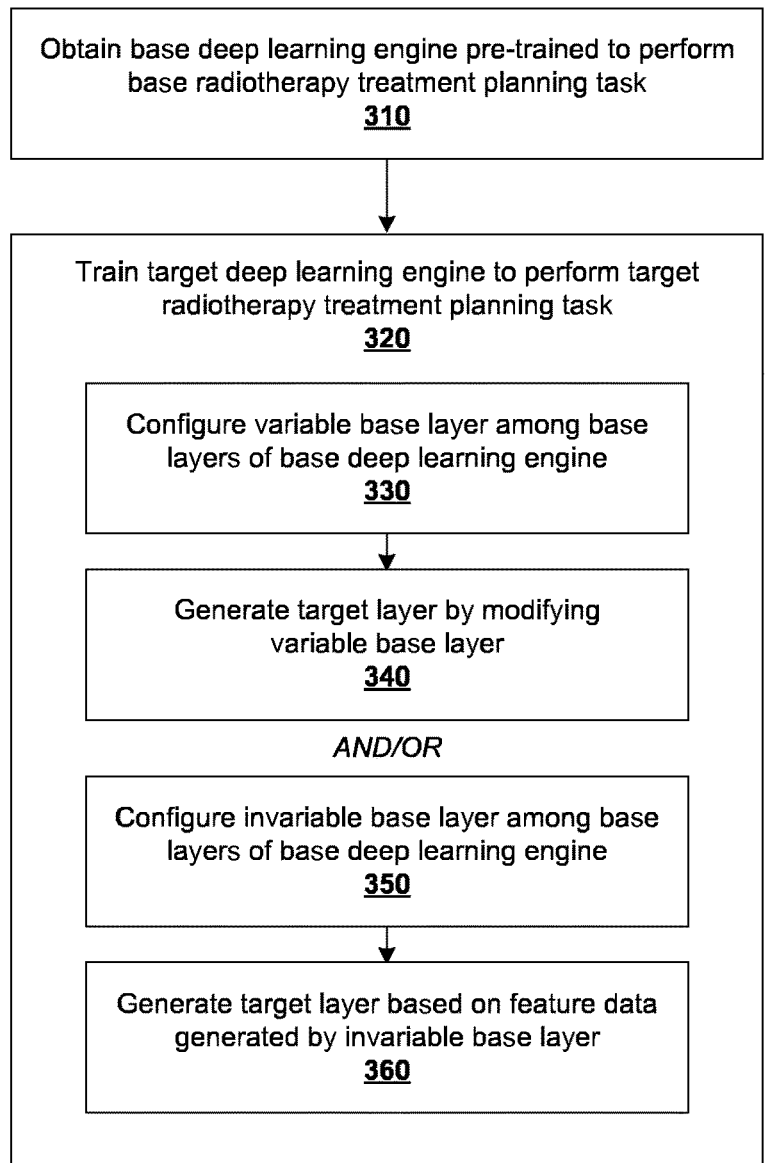

Obtain base deep learning engine pre-trained to perform
base radiotherapy treatment planning task
310

Train target deep learning engine to perform target
radiotherapy treatment planning task
320

Configure variable base layer among base
layers of base deep learning engine
330

Generate target layer by modifying
variable base layer
340

*AND/OR*

Configure invariable base layer among base
layers of base deep learning engine
350

Generate target layer based on feature data
generated by invariable base layer
360

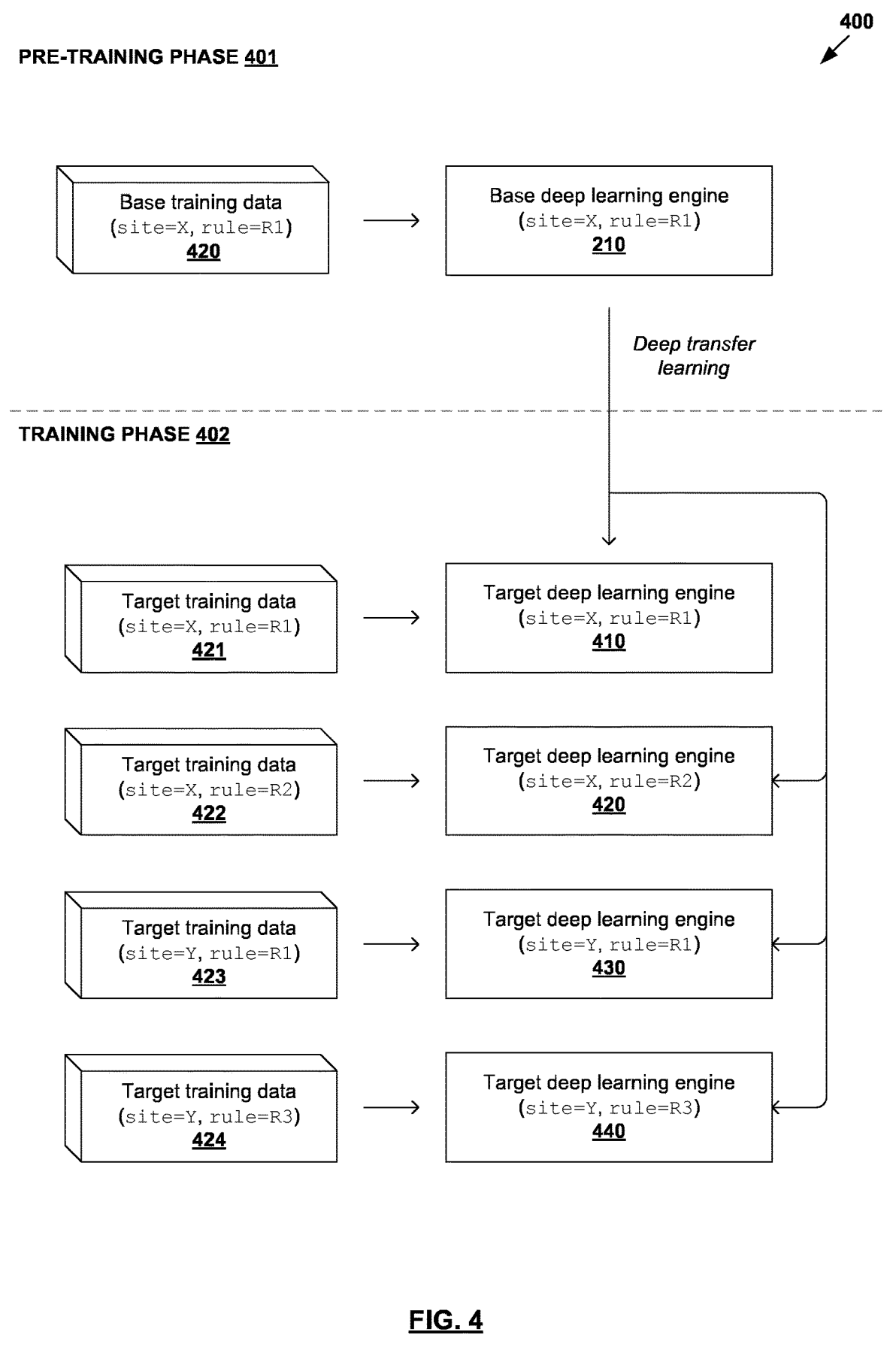

PRE-TRAINING PHASE 401

Base training data
(site=X, rule=R1)
420

→

Base deep learning engine
(site=X, rule=R1)
210

*Deep transfer learning*

TRAINING PHASE 402

Target training data
(site=X, rule=R1)
421

→

Target deep learning engine
(site=X, rule=R1)
410

Target training data
(site=X, rule=R2)
422

→

Target deep learning engine
(site=X, rule=R2)
420

Target training data
(site=Y, rule=R1)
423

→

Target deep learning engine
(site=Y, rule=R1)
430

Target training data
(site=Y, rule=R3)
424

→

Target deep learning engine
(site=Y, rule=R3)
440

FIG. 4

PRE-TRAINING PHASE 501                                                                                      500

TRAINING PHASE 502

PRE-TRAINING PHASE 701                                                    700

TRAINING PHASE 702

INFERENCE PHASE 801

156/900

1000

1033 REQUEST TARGET(X,D2)

User Device (CLI) 1003

1043 RESPONSE

Planning System 1010

Data Tier 1013 ↔ Training Infra. 1012 ↔ UI Tier 1011

1032 REQUEST TARGET(Y,R1)

User Device (API) 1002

1042 RESPONSE

Datastore 1020

| Base engine (ID=100) | 1021 |
| ... | |
| Base engine (ID=150) | 1022 |
| Target engine (ID=200) | 1023 |
| ... | |
| Target engine (ID=299) | 1024 |

1031 REQUEST TARGET(X,R2)

User Device (GUI) 1001

1041 RESPONSE

1100

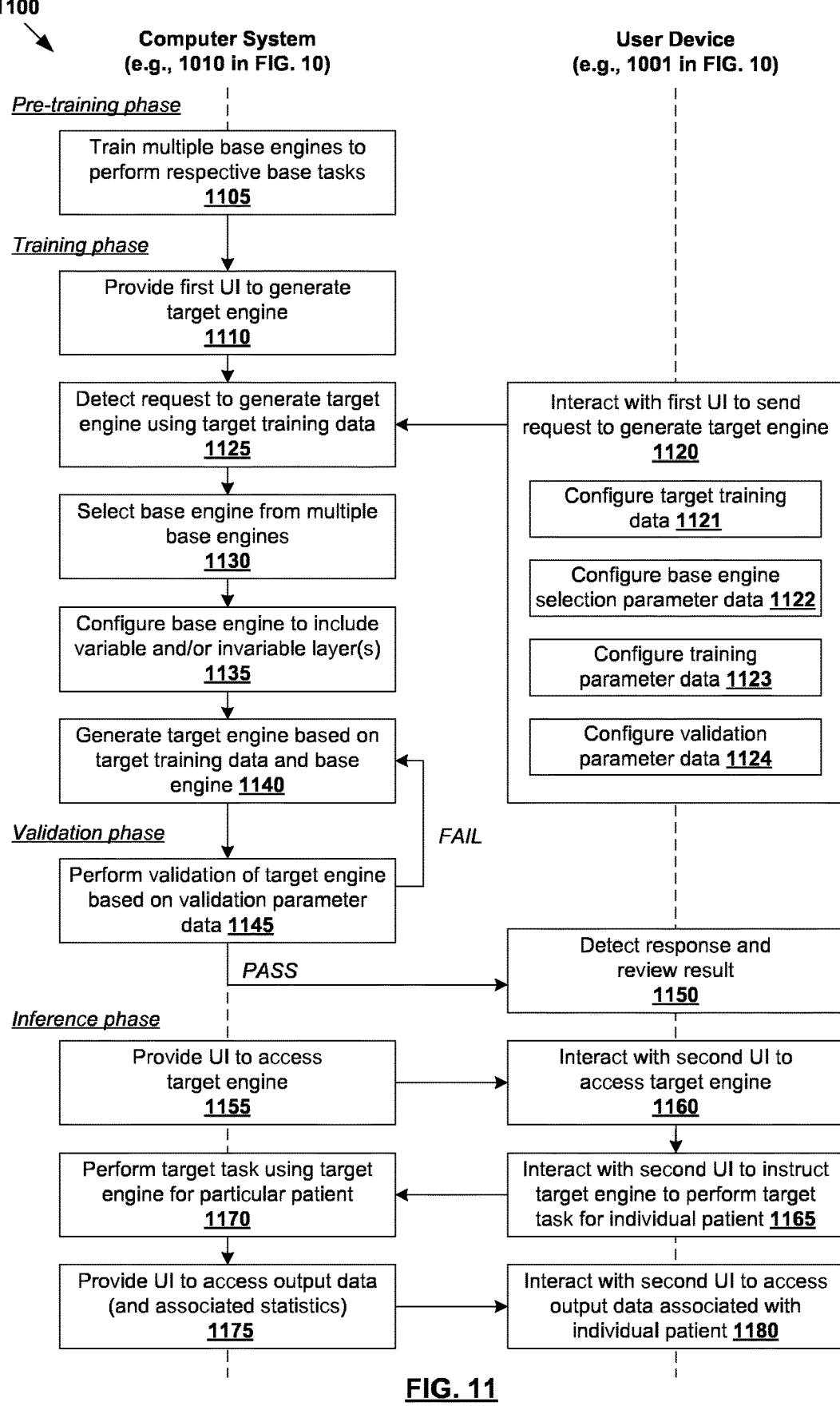

Computer System
(e.g., 1010 in FIG. 10)

User Device
(e.g., 1001 in FIG. 10)

*Pre-training phase*

Train multiple base engines to perform respective base tasks
1105

*Training phase*

Provide first UI to generate target engine
1110

Detect request to generate target engine using target training data
1125

Interact with first UI to send request to generate target engine
1120

Configure target training data 1121

Configure base engine selection parameter data 1122

Configure training parameter data 1123

Configure validation parameter data 1124

Select base engine from multiple base engines
1130

Configure base engine to include variable and/or invariable layer(s)
1135

Generate target engine based on target training data and base engine 1140

*Validation phase*

*FAIL*

Perform validation of target engine based on validation parameter data 1145

*PASS*

Detect response and review result
1150

*Inference phase*

Provide UI to access target engine
1155

Interact with second UI to access target engine
1160

Perform target task using target engine for particular patient
1170

Interact with second UI to instruct target engine to perform target task for individual patient 1165

Provide UI to access output data (and associated statistics)
1175

Interact with second UI to access output data associated with individual patient 1180

FIG. 11

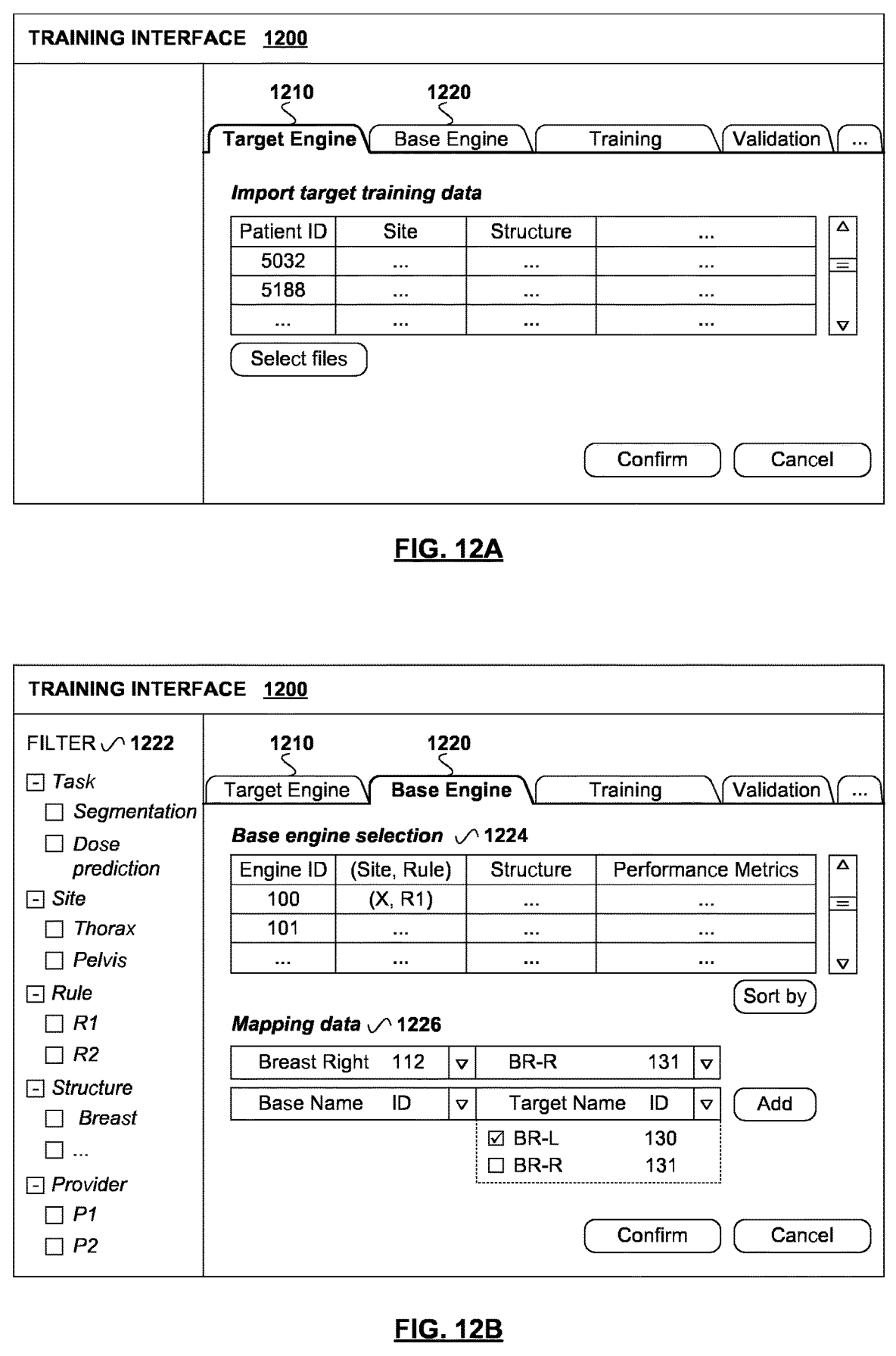

TRAINING INTERFACE <u>1200</u>

1210        1220

| Target Engine | Base Engine | Training | Validation | ... |

*Import target training data*

| Patient ID | Site | Structure | ... | |
|---|---|---|---|---|
| 5032 | ... | ... | ... | △ |
| 5188 | ... | ... | ... | ≡ |
| ... | ... | ... | ... | ▽ |

( Select files )

( Confirm )  ( Cancel )

TRAINING INTERFACE <u>1200</u>

FILTER ⌇ 1222

⊟ *Task*
  ☐ *Segmentation*
  ☐ *Dose*
    *prediction*
⊟ *Site*
  ☐ *Thorax*
  ☐ *Pelvis*
⊟ *Rule*
  ☐ *R1*
  ☐ *R2*
⊟ *Structure*
  ☐ *Breast*
  ☐ *...*
⊟ *Provider*
  ☐ *P1*
  ☐ *P2*

1210      1220

| Target Engine | Base Engine | Training | Validation | ... |

Base engine selection ⌇ 1224

| Engine ID | (Site, Rule) | Structure | Performance Metrics | |
|---|---|---|---|---|
| 100 | (X, R1) | ... | ... | △ |
| 101 | ... | ... | ... | ≡ |
| ... | ... | ... | ... | ▽ |

( Sort by )

Mapping data ⌇ 1226

| Breast Right | 112 | ▽ | BR-R | 131 | ▽ |

| Base Name | ID | ▽ | Target Name | ID | ▽ | ( Add ) |

☑ BR-L    130
    ☐ BR-R    131

( Confirm )  ( Cancel )

FIG. 12B

TRAINING INTERFACE <u>1200</u>

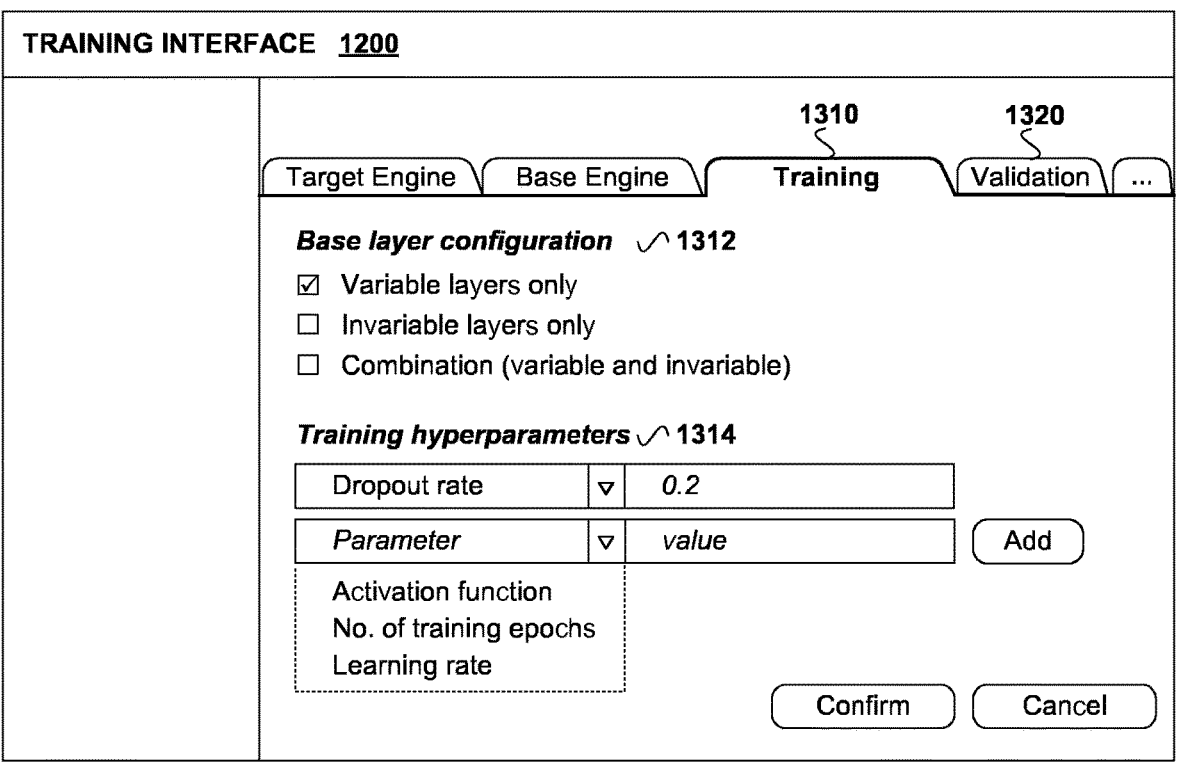

1310    1320

| Target Engine | Base Engine | Training | Validation | ... |

*Base layer configuration* ✓∧ 1312

☑ Variable layers only

☐ Invariable layers only

☐ Combination (variable and invariable)

*Training hyperparameters* ✓∧ 1314

| Dropout rate | ▽ | *0.2* |
| *Parameter* | ▽ | *value* | Add |

Activation function
No. of training epochs
Learning rate ( Confirm )    ( Cancel )

FIG. 13A

TRAINING INTERFACE <u>1200</u>

1310    1320

| Target Engine | Base Engine | Training | Validation | ... |

*Validation criteria* ✓∧ 1322

☑ Dice score                          *threshold* △

☑ Average surface difference   *threshold* ≡

☐ ...                                      ...

☐ ...                                      ...

☑ Hausdorff distance             *threshold* ▽

( Confirm )    ( Cancel )

FIG. 13B

1600
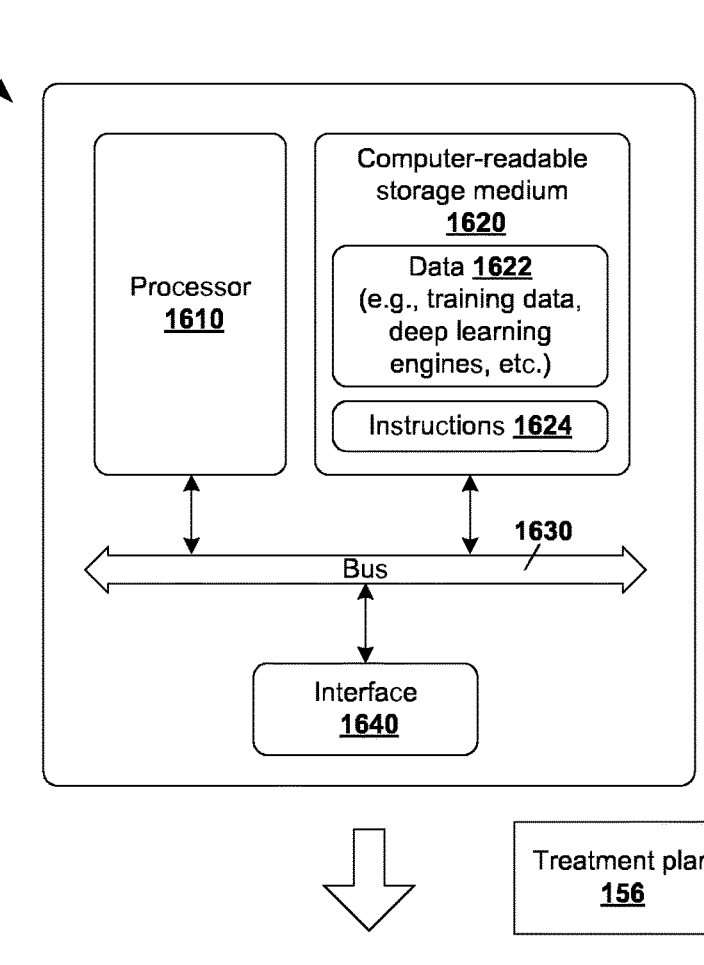
Treatment plan
156
160
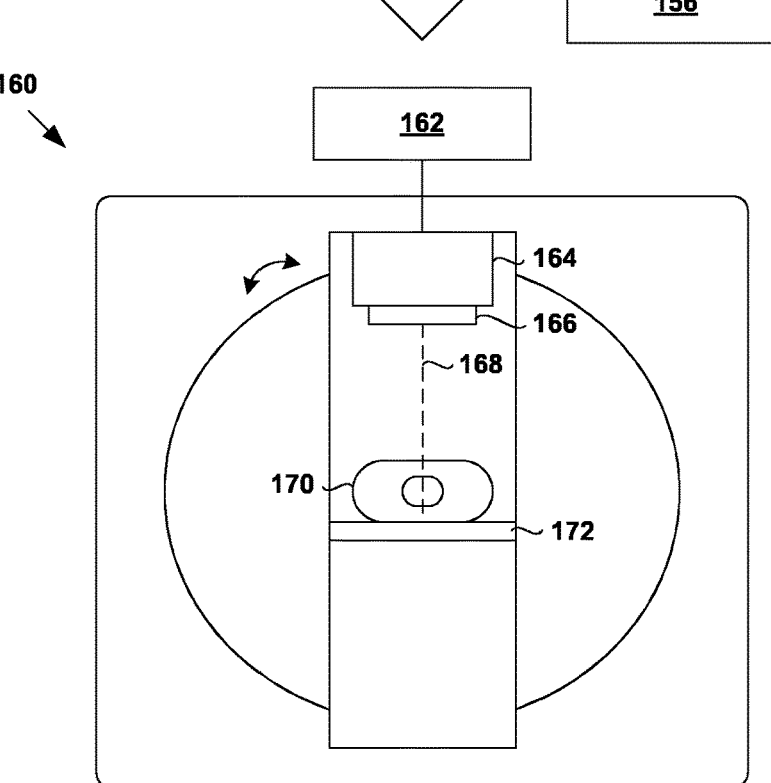
FIG. 16

METHODS AND SYSTEMS FOR RADIOTHERAPY TREATMENT PLANNING BASED ON DEEP TRANSFER LEARNING

CROSS-REFERENCE TO RELATED APPLICATIONS

The present application is a 371 application of International Application PCT/EP2019/064145, filed on May 30, 2019 and entitled "METHODS AND SYSTEMS FOR RADIOTHERAPY TREATMENT PLANNING BASED ON DEEP TRANSFER LEARNING." The International application claims the benefit of U.S. Provisional Application No. 62/783,217 filed on Dec. 21, 2018. The present application is related in subject matter to U.S. patent application Ser. No. 16/145,461. The aforementioned applications, including any appendices or attachments thereof, are hereby incorporated by reference in their entirety.

BACKGROUND

Unless otherwise indicated herein, the approaches described in this section are not prior art to the claims in this application and are not admitted to be prior art by inclusion in this section.

Radiotherapy is an important part of a treatment for reducing or eliminating unwanted tumors from patients. Unfortunately, applied radiation does not inherently discriminate between an unwanted tumor and any proximal healthy structures such as organs, etc. This necessitates careful administration to restrict the radiation to the tumor (i.e., target). Ideally, the goal is to deliver a lethal or curative radiation dose to the tumor, while maintaining an acceptable dose level in the proximal healthy structures. However, to achieve this goal, conventional radiotherapy treatment planning may be time and labor intensive.

SUMMARY

According to examples of the present disclosure, methods and systems for deep transfer learning for radiotherapy treatment planning are provided. One example method may comprise: obtaining a base deep learning engine that is pre-trained to perform a base radiotherapy treatment planning task; and based on the base deep learning engine, generating a target deep learning engine to perform a target radiotherapy treatment planning task. The target deep learning engine may be generated by configuring a variable base layer among multiple base layers of the base deep learning engine, and generating one of multiple target layers of the target deep learning engine by modifying the variable base layer. Alternatively or additionally, the target deep learning engine may be generated by configuring an invariable base layer among the multiple base layers, and generating one of multiple target layers of the target deep learning engine based on feature data generated using the invariable base layer. Various examples will be discussed below, such as with reference to FIGS. 1-9 and 16.

According to examples of the present disclosure, methods and systems for radiotherapy treatment planning based on deep transfer learning are provided. One example method may comprise: providing a first user interface for sending a request to generate a target deep learning engine to perform a target radiotherapy treatment planning task. In response to detecting, via the first user interface, the request to generate the target deep learning engine, a base deep learning engine may be selected from multiple base deep learning engines that are pre-trained to perform respective base radiotherapy treatment planning tasks. Based on the selected base deep learning engine and target training data associated with multiple past patients, the target deep learning engine may be generated to perform the target radiotherapy treatment planning task. The method may also comprise: providing a second user interface for accessing the target deep learning engine to perform the target radiotherapy treatment planning task for an individual patient. Various examples will be discussed below, such as with reference to FIGS. 10-15B and 16.

BRIEF DESCRIPTION OF THE DRAWINGS

FIG. 2 is a schematic diagram illustrating example deep transfer learning for radiotherapy treatment planning;

FIG. 3 is a flowchart of an example process for a computer system to perform deep transfer learning for radiotherapy treatment planning;

FIG. 4 is a schematic diagram illustrating example deep transfer learning according to the example in FIG. 3;

FIG. 11 is a flowchart of an example process for deep transfer learning for radiotherapy treatment planning using the example in FIG. 10;

FIG. 12A is schematic diagram illustrating a first example interface for target engine generation during training phase;

FIG. 12B is schematic diagram illustrating a second example interface for target engine generation during training phase;

FIG. 13A is schematic diagram illustrating a third example interface for target engine generation during training phase;

FIG. 13B is schematic diagram illustrating a fourth example interface for target engine generation during training phase;

FIG. 16 is a schematic diagram of an example computer system to perform deep transfer learning for radiotherapy treatment planning.

DETAILED DESCRIPTION

The technical details set forth in the following description enable a person skilled in the art to implement one or more embodiments of the present disclosure.

Figure 1:
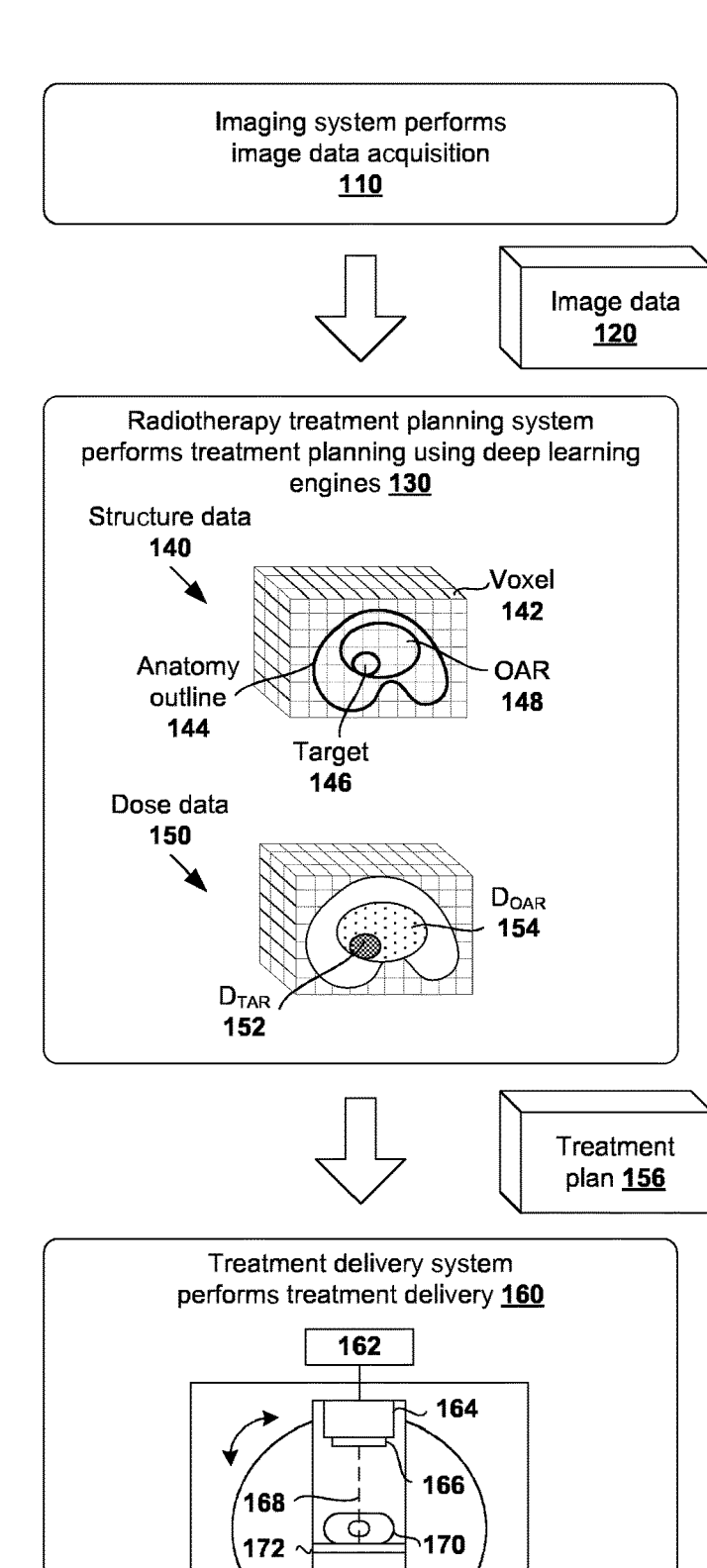
FIG. 1 is a schematic diagram illustrating an example process flow for radiotherapy treatment.

FIG. 1 is a schematic diagram illustrating example process flow 100 for radiotherapy treatment. Example process 100 may include one or more operations, functions, or actions illustrated by one or more blocks. The various blocks may be combined into fewer blocks, divided into additional blocks, and/or eliminated based upon the desired implementation. In the example in FIG. 1, radiotherapy treatment generally includes various stages, such as an imaging system performing image data acquisition for a patient (see 110); a radiotherapy treatment planning system (see 130) generating a suitable treatment plan (see 156) for the patient; and a treatment delivery system (see 160) delivering treatment according to the treatment plan.

In more detail, at 110 in FIG. 1, image data acquisition may be performed using an imaging system to capture image data 120 associated with a patient (particularly the patient's anatomy). Any suitable medical image modality or modalities may be used, such as computed tomography (CT), cone beam computed tomography (CBCT), positron emission tomography (PET), magnetic resonance imaging (MRI), single photon emission computed tomography (SPECT), any combination thereof, etc. For example, when CT or MRI is used, image data 120 may include a series of two-dimensional (2D) images or slices, each representing a cross-sectional view of the patient's anatomy, or may include volumetric or three-dimensional (3D) images of the patient, or may include a time series of 2D or 3D images of the patient (e.g., four-dimensional (4D) CT or 4D CBCT).

At 130 in FIG. 1, radiotherapy treatment planning may be performed during a planning phase to generate treatment plan 156 based on image data 120. Any suitable number of treatment planning tasks or steps may be performed, such as segmentation, dose prediction, projection data prediction, treatment plan generation, etc. For example, segmentation may be performed to generate structure data 140 identifying various segments or structures may from image data 120. In practice, a three-dimensional (3D) volume of the patient's anatomy may be reconstructed from image data 120. The 3D volume that will be subjected to radiation is known as a treatment or irradiated volume that may be divided into multiple smaller volume-pixels (voxels) 142. Each voxel 142 represents a 3D element associated with location (i, j, k) within the treatment volume. Structure data 140 may be include any suitable data relating to the contour, shape, size and location of patient's anatomy 144, target 146, organ-at-risk (OAR) 148, or any other structure of interest (e.g., tissue, bone). For example, using image segmentation, a line may be drawn around a section of an image and labelled as target 146 (e.g., tagged with label="prostate"). Everything inside the line would be deemed as target 146, while everything outside would not.

In another example, dose prediction may be performed to generate dose data 150 specifying radiation dose to be delivered to target 146 (denoted "$D_{TAR}$" at 152) and radiation dose for OAR 148 (denoted "$D_{OAR}$" at 154). In practice, target 146 may represent a malignant tumor (e.g., prostate tumor, etc.) requiring radiotherapy treatment, and OAR 148 a proximal healthy structure or non-target structure (e.g., rectum, bladder, etc.) that might be adversely affected by the treatment. Target 146 is also known as a planning target volume (PTV). Although an example is shown in FIG. 1, the treatment volume may include multiple targets 146 and OARs 148 with complex shapes and sizes. Further, although shown as having a regular shape (e.g., cube), voxel 142 may have any suitable shape (e.g., non-regular). Depending on the desired implementation, radiotherapy treatment planning at block 130 may be performed based on any additional and/or alternative data, such as prescription, disease staging, biologic or radiomic data, genetic data, assay data, biopsy data, past treatment or medical history, any combination thereof, etc.

Based on structure data 140 and dose data 150, treatment plan 156 may be generated include 2D fluence map data for a set of beam orientations or angles. Each fluence map specifies the intensity and shape (e.g., as determined by a multileaf collimator (MLC)) of a radiation beam emitted from a radiation source at a particular beam orientation and at a particular time. For example, in practice, intensity modulated radiotherapy treatment (IMRT) or any other treatment technique(s) may involve varying the shape and intensity of the radiation beam while at a constant gantry and couch angle. Alternatively or additionally, treatment plan 156 may include machine control point data (e.g., jaw and leaf positions), volumetric modulated arc therapy (VMAT) trajectory data for controlling a treatment delivery system, etc. In practice, block 130 may be performed based on goal doses prescribed by a clinician (e.g., oncologist, dosimetrist, planner, etc.), such as based on the clinician's experience, the type and extent of the tumor, patient geometry and condition, etc.

At 160 in FIG. 1, treatment delivery is performed during a treatment phase to deliver radiation to the patient according to treatment plan 156. For example, radiotherapy treatment delivery system 160 may include rotatable gantry 164 to which radiation source 166 is attached. During treatment delivery, gantry 164 is rotated around patient 170 supported on structure 172 (e.g., table) to emit radiation beam 168 at various beam orientations according to treatment plan 156. Controller 162 may be used to retrieve treatment plan 156 and control gantry 164, radiation source 166 and radiation beam 168 to deliver radiotherapy treatment according to treatment plan 156.

It should be understood that any suitable radiotherapy treatment delivery system(s) may be used, such as mechanic-arm-based systems, tomotherapy type systems, brachy therapy, sirex spheres, any combination thereof, etc. Additionally, examples of the present disclosure may be applicable to particle delivery systems (e.g., proton, carbon ion, etc.). Such systems may employ either a scattered particle beam that is then shaped by a device akin to an MLC, or a scanning beam of adjustable energy, spot size and dwell time. Also, OAR segmentation might be performed, and automated segmentation of the applicators might be desirable.

Conventionally, radiotherapy treatment planning at block 130 in FIG. 1 is time and labor intensive. For example, it usually requires a team of highly skilled and trained oncologists and dosimetrists to manually delineate structures of interest by drawing contours or segmentations on image data 120. These structures are manually reviewed by a physician, possibly requiring adjustment or re-drawing. In many cases, the segmentation of critical organs can be the most time-consuming part of radiation treatment planning. After the structures are agreed upon, there are additional labor-intensive steps to process the structures to generate a clinicallyoptimal treatment plan specifying treatment delivery data such as beam orientations and trajectories, as well as corresponding 2D fluence maps. These steps are often complicated by a lack of consensus among different physicians and/or clinical regions as to what constitutes "good" contours or segmentation. In practice, there might be a huge variation in the way structures or segments are drawn by different clinical experts. The variation may result in uncertainty in target volume size and shape, as well as the exact proximity, size and shape of OARs that should receive minimal radiation dose. Even for a particular expert, there might be variation in the way segments are drawn on different days.

According to examples of the present disclosure, artificial intelligence (AI) techniques may be applied to ameliorate various challenges associated with radiotherapy treatment planning. In particular, deep learning engine(s) may be used to automate radiotherapy treatment planning step(s). Throughout the present disclosure, the term "deep learning" may refer generally to a class of approaches that utilizes many layers or stages of nonlinear data processing for feature learning as well as pattern analysis and/or classification. The "deep learning model" may refer to a hierarchy of "layers" of nonlinear data processing that include an input layer, an output layer, and multiple (i.e., two or more) "hidden" layers between the input and output layers. These layers may be trained from end-to-end (e.g., from the input layer to the output layer) to extract feature(s) from an input and classify the feature(s) to produce an output (e.g., classification label or class).

Accordingly, the term "deep learning engine" may refer to any suitable hardware and/or software component(s) of a computer system that are capable of executing algorithms according to any suitable deep learning model(s). Depending on the desired implementation, any suitable deep learning model(s) may be used, such as convolutional neural network, recurrent neural network, deep belief network, generative adversarial network (GAN), or any combination thereof, etc. In practice, a neural network is generally formed using a network of processing elements (called "neurons," "nodes," etc.) that are interconnected via connections (called "synapses," "weights," etc.). For example, convolutional neural networks may be implemented using any suitable architecture(s), such as U-net, LeNet, AlexNet, ResNet, V-net, DenseNet, etc. In this case, a "layer" of a convolutional neural network may be a convolutional layer, pooling layer, rectified linear units (ReLU) layer, fully connected layer, loss layer, activation layer, dropout layer, transpose convolutional layer, concatenation layer, or any combination thereof, etc. In practice, the U-net architecture includes a contracting path (left side) and an expansive path (right side). The contracting path includes repeated application of convolutions, followed by a ReLU layer and max pooling layer. Each step in the expansive path may include upsampling or transpose convolutions of the feature map followed by convolutions, etc.

Deep learning approaches should be contrasted against machine learning approaches that have been applied to, for example, automatic segmentation. In general, these approaches involve extracting (hand-designed) feature vectors from images, such as for every voxel, etc. Then, the feature vectors may be used as input to a machine learning model that classifies which class each voxel belongs to. However, such machine learning approaches usually do not make use of complete image data and additional constraints may be required. Another challenge is that these approaches rely on a high dimension of hand-designed features in order to accurately predict the class label for each voxel. Solving a high-dimensional classification problem is computationally expensive and requires a large amount of memory. Some approaches use lower dimensional features (e.g., using dimensionality reduction techniques) but they may decrease the prediction accuracy.

Conventionally, there are many challenges associated with training deep learning engines for radiotherapy treatment planning. For example, it may be difficult to achieve desirable training results for deep learning engines without regularizing the training process and/or collecting a huge amount of curated training data. This may lead suboptimal results or, worse, failure to create any working deep learning engines. In another example, if inexperienced users (e.g., clinicians) are provided with a tool to train their own deep learning engines, it can be challenging to perform the training from scratch. For example, in relation to automatic segmentation, the computational cost of training a blank deep learning engine can be high, especially if a large number of anatomical structures need to be modelled.

While conceptually simple, training deep learning engines generally requires significant technical expertise relating to model architecture(s), optimization, convergence analysis, regularization, etc. When trained with a limited amount of data, a deep learning engine that starts with a blank state may diverge to a suboptimal form. Such complexity of the training process may deter users from training and using deep learning engines for radiotherapy treatment planning, which is undesirable.

Deep Transfer Learning

According to examples of the present disclosure, deep transfer learning may be performed to improve the training process of deep learning engines for radiotherapy treatment planning. Instead of starting from scratch using a blank state with random weights, a pre-trained "base" deep learning engine may be used as a starting point to improve the training phase of a "target" deep learning engine, particularly with reduced resources in terms of both computing and personnel. The target deep learning engine may be adapted from the base learning engine to according to any suitable users' needs and specifications.

As used herein, the term "deep transfer learning" may refer generally to technique(s) where one deep learning engine is adapted or re-purposed (fully or partially) as a starting point for another deep learning engine. In practice, deep transfer learning represents an optimization strategy that facilitates faster progress or improved performance during the training process. By improving the efficiency of radiotherapy treatment planning using deep transfer learning, treatment outcome may also be improved for patients, such as increasing the tumor control probability and/or reducing the likelihood of health complications or death due to radiation overdose in the healthy structures, etc.

In more detail, FIG. 2 is a schematic diagram illustrating example deep transfer learning 200 for radiotherapy treatment planning. In particular, deep transfer learning may be performed from a base deep learning engine (see 210) to a target deep learning engine (see 220, 230 and 240). Base deep learning engine 210 may represent a "pre-trained model" that is generated or trained during pre-training phase 201 based on base training data 203 (e.g., performed at a provider's site). Target deep learning engine 220/230/240 may be generated or trained based on base deep learning engine 210 and target training data that is available during subsequent training phase 202 (e.g., performed at a user's site).

Examples of the present disclosure may be implemented to ameliorate various challenges associated with training deep learning engines for radiotherapy treatment planning. In one example, users do not have to start training target deep learning engine 220/230/240 from scratch, especially when they only have a limited amount of target training data (e.g., limited in amount or variations) that may lead to suboptimal results. Instead, users may take advantage of the better quality base training data 203 (e.g., more data, availability of expert-curated data, more variations, etc.) used to train base deep learning engine 210.

Further, the computational cost of training deep learning engine 220/230/240 for radiotherapy treatment planning may be reduced by taking advantage of the knowledge already learned by base deep learning engine 210. This helps increase the rate of improvement and convergence of target deep learning engine 220/230/240 during training phase 202. The risk of achieving suboptimal training results due to limited training data (e.g., limited in amount or variation) may also be reduced. Using examples of the present disclosure, it is not necessary for users (e.g., clinicians) to have extensive knowledge about deep learning model architecture(s), etc. For example, by providing substantially stable base deep learning engine 210, the required knowledge of the clinicians related to technical issues such as convergence, local minima or poor weight initializations during training phase 202 may be reduced.

Some examples will be discussed using FIG. 3, which is a flowchart of example process 300 for a computer system to deep transfer learning for radiotherapy treatment planning. Example process 300 may include one or more operations, functions, or actions illustrated by one or more blocks, such as 310 to 360. The various blocks may be combined into fewer blocks, divided into additional blocks, and/or eliminated based upon the desired implementation. Example process 300 may be implemented using any suitable computer system(s), an example of which will be discussed using FIG. 16.

At 310 in FIG. 3, base deep learning engine 210 that is pre-trained to perform a base radiotherapy treatment planning task may be obtained. Here, the term "obtain" may refer generally to a computer system accessing, or retrieving data and/or computer-readable instructions associated with, base deep learning engine 210 from any suitable source (e.g., another computer system), memory or datastore (e.g., local or remote), etc. Base deep learning engine 210 may include multiple (N) base layers (denoted as $B_i$, where i=1, ..., N) to perform a base radiotherapy treatment planning task. In the case of N=4 in FIG. 2, base deep learning engine 210 includes four base layers 211-214.

At 320 in FIG. 3, based on base deep learning engine 220, target deep learning engine 220/230/240 may be generated to perform a target radiotherapy treatment planning task. Target deep learning engine 220/230/240 may include multiple (M) target layers (denoted as $T_j$, where j=1, ..., M). It should be noted that M (i.e., the number of target layers) may be the same as, or different from, N (i.e., the number of base layers). As such, base deep learning engine 210 may be further trained to suit the users' needs, or fixed and used as is. Base layers 211-214 of base engine 200 may be configured to be variable (see 330 and 340), invariable (see 350 and 360), or a combination of both.

In a first example, based on configuration of a variable base layer among base layers 211-214, a target layer may be generated by modifying the variable base layer according to 330-340 in FIG. 3. Here, the term "variable" may refer to a layer whose weights are modifiable during training phase 202. For example in FIG. 2, base layers 211-214 may be configured to be variable to generate first target deep learning engine 220. Based on configuration of variable base layers 211-214, target layers 221-224 may be generated by modifying respective variable base layers 211-214. See also 250 and symbol "→>" indicating modification.

In a second example, based on configuration of an invariable base layer among base layers 211-214, a target layer may be generated based on feature data generated using the invariable base layer according to 350-360 in FIG. 3. Here, the term "invariable" may refer to a layer whose weights are fixed and not modified during training phase 202. For example in FIG. 2, base layers 211-214 may be configured to be invariable to generate second target deep learning 230. This way, target layers 231-233 may be trained based on feature data (denoted $F_i$, where i=1, N=4) generated by invariable base layers 211-214.

In a third example, a combination of variable and invariable base layers may be used to generate third target deep learning engine 240 in FIG. 2. In this case, base layers 211-212 may be configured to be invariable and remaining base layers 213-214 variable. The latter variable base layers 213-214 may then be modified to generate respective target layers 241-242. Additional target layers 243-245 may be generated or trained based on feature data (denoted $F_1$ and $F_2$) generated using respective invariable base layers 211-212. As will be discussed using FIGS. 4-6, a continuum of target deep learning engines may be generated using different combinations of variable and invariable base layers.

Depending on the desired implementation, base deep learning engine 210 and target deep learning engine 220/230/240 may be trained to perform any suitable radiotherapy treatment planning task(s), such as automatic segmentation, dose prediction, treatment delivery data estimation, abnormal organ detection, treatment outcome prediction, or any combination thereof. In the case of automatic segmentation, engine 210/220/230/240 may be trained to generate output=structure data (e.g., 140 in FIG. 1) based on input=image data (e.g., 120 in FIG. 1). In the case of dose prediction, engine 210/220/230/240 may be trained to generate output=dose data (e.g., 150 in FIG. 1) based on input=structure data and beam geometry data. In the case of treatment delivery data estimation, engine 210/220/230/240 may be trained to generate output=treatment delivery data (e.g., fluence map data, structure projection data, etc.) based on input=structure data and/or dose data, etc.

Further, base and target deep learning engines may each be trained to perform radiotherapy treatment planning task(s) associated with any suitable anatomical site(s), rule(s), etc. Some examples are shown in FIG. 4, which is a schematic diagram illustrating example deep transfer learning 400 according to the example in FIG. 3. In the examples in FIG. 4, base deep learning engine 210 may be trained using base training data 420 to perform a base radiotherapy treatment planning task associated with a base anatomical site=X (e.g., bladder region) and a base rule=R1 according to which the task is performed.

Based on base deep learning engine 210, target deep learning engines 410-440 may be generated to perform a target radiotherapy treatment planning task associated with the same anatomical site=X (see 410-420), or a different anatomical site=Y (see 430-440). Further, target deep learning engines 410-440 associated with the same rule=R1 (see 410, 430) or a different rule=R2 or R3 (see 420, 440) may be generated. Here, the term "anatomical site" or "anatomical region" may refer generally to one part of a patient's anatomy that has been captured using imaging modality or modalities. The term "rule" may refer to any suitable clinical guideline(s), strategy and/or planning practice(s) relating to a particular radiotherapy treatment planning task. To repurpose base deep learning engine 210, target training data 421-424 associated with the target anatomical site (e.g., X or Y) and/or rule (e.g., R1, R2 or R3) may be used during training phase 402. This way, base deep learning engine 210 may be adapted according to the users' needs and specifications.

In the following, various examples will be discussed below using FIG. 5 to FIG. 11. In particular, deep transfer learning for automatic segmentation will be discussed using FIGS. 5-6, and dose prediction using FIG. 7. Example inference phase will be explained using FIGS. 8-9 and example computer system using FIG. 16. For simplicity, "deep learning engine" will be referred to as "engine" (e.g., base engine and target engine), and "radiotherapy treatment planning task" as "task" (e.g., base task and target task).

Automatic Segmentation

Figure 5:
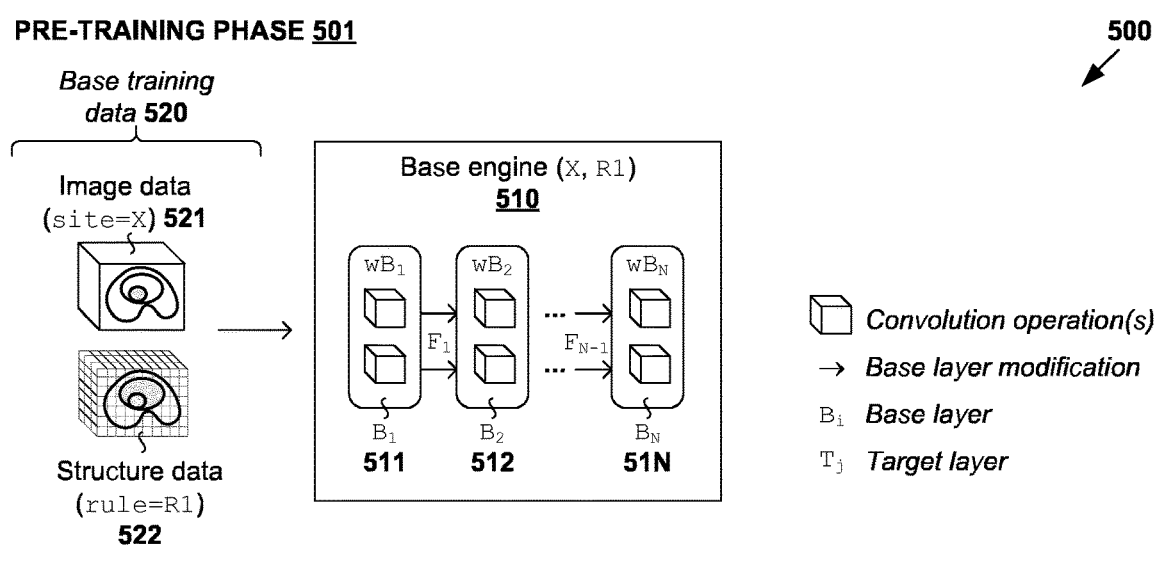
FIG. 5 is a schematic diagram illustrating first example deep transfer learning for automatic segmentation of image data.
Figure 6:
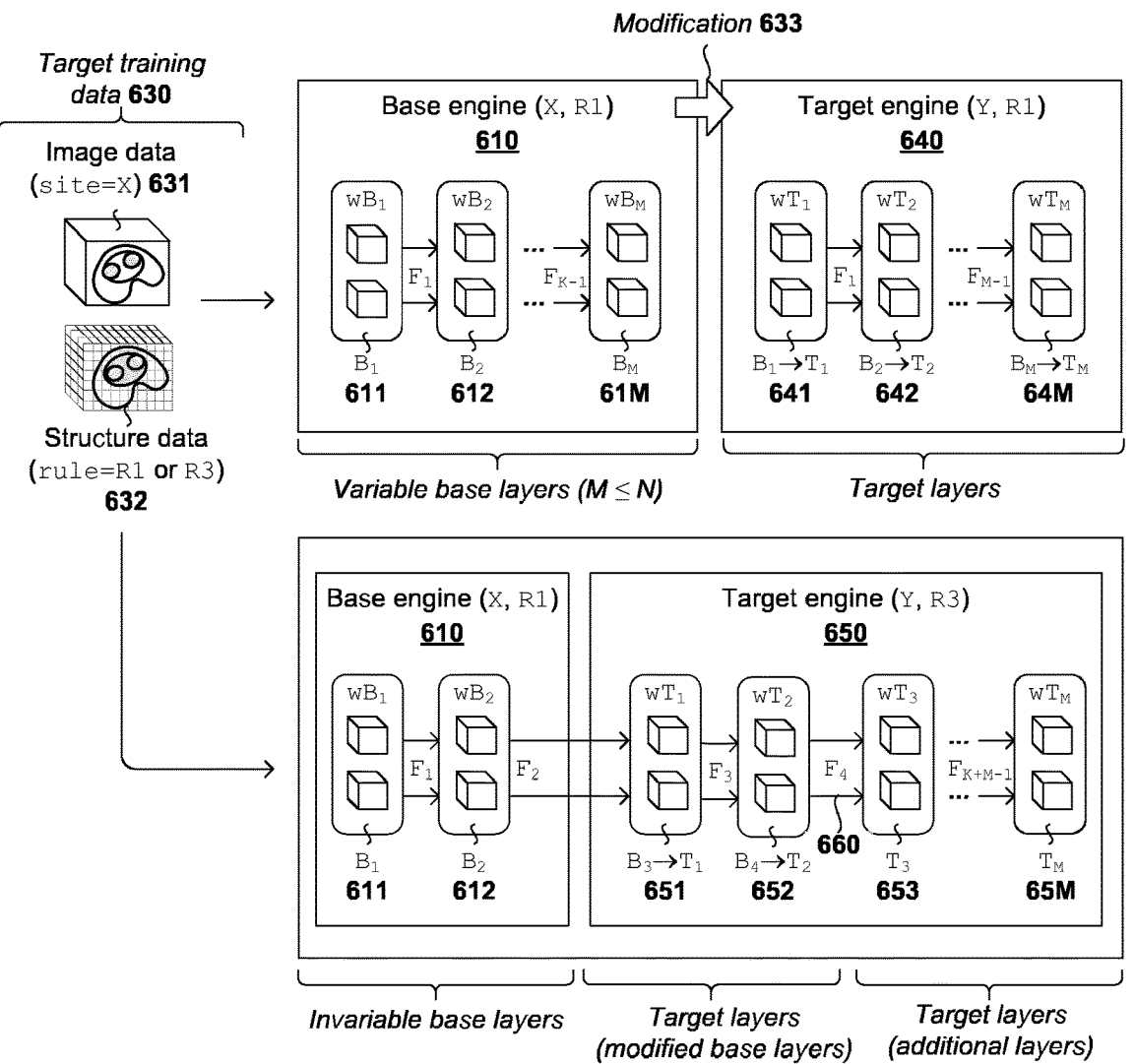
FIG. 6 is a schematic diagram illustrating second example deep transfer learning for automatic segmentation of image data.

FIG. 5 is a schematic diagram illustrating first example deep transfer learning 500 for automatic segmentation of image data, and FIG. 6 a schematic diagram illustrating second example deep transfer learning 600 for automatic segmentation of image data. In both examples, base engine 510/610 may be pre-trained to perform base task=automatic segmentation for a base anatomical site (e.g., X=breast region) according to a base segmentation rule (e.g., R1=segmentation margin of 2 mm). The knowledge learned by base engine 510/610 may be transferred to various target engines during subsequent training phase 502/602.

In the examples in FIG. 5, target engines 540-550 are trained to perform target task=automatic segmentation for the same anatomical site as base engine 510, but according to a different target rule (e.g., R2=contouring margin of 5 mm). In the examples in FIG. 6, target engines 640-650 are trained to perform target task=automatic segmentation for a different target anatomical site (e.g., Y=lung region) compared to base engine 610. The examples will be discussed in turn below. In practice, the result of automatic segmentation may be used for abnormal organ detection, dose prediction, treatment delivery data estimation, etc.

Although exemplified using segmentation margin in the following examples, it should be understood that the base and target segmentation rules (e.g., R1 and R2) may be configured based on any suitable segmentation or contouring guidelines, such as when a structure stops, etc. For example, the contouring guidelines specifying when to stop contouring a structure (e.g., breast) superiorly and inferiorly, or whether the contour ends at the skin boundary or extends to the fat tissue (e.g., in the case of pendulum breast). Any additional and/or base and target segmentation rules may be used in the following examples.

(a) Base Engine (Site=X, Rule R1)

Referring first to in FIG. 5, base engine 510 may be trained during pre-training phase 501 using any suitable base training data 521-522 associated with (site=X, rule R1). The aim of pre-training phase 501 is to train base engine 510 to perform automatic segmentation by mapping input training data=image data 521 to output training data=structure data 522. In practice, image data 521 may include 2D or 3D images of the patient's anatomical site, and captured using any suitable imaging modality or modalities. Structure data 522 may identify any suitable contour, shape, size and/or location of structure(s) identifiable from image data 521. Example structures may include target(s), OAR(s) or any other structure of interest (e.g., tissue, bone).

For example, in relation to prostate cancer, image data 521 may include image data of X=prostate region. In this case, structure data 522 may identify a target representing the patient's prostate, and OARs representing proximal healthy structures such as rectum and bladder. In relation to lung cancer treatment, image data 521 may include image data of X=lung region. In this case, structure data 522 may identify a target representing cancerous lung tissue, and an OAR representing proximal healthy lung tissue, esophagus, heart, etc. In relation to brain cancer, image data 521 may include image data of X=brain region, in which case structure data 522 may identify a target representing a brain tumor, and an OAR representing a proximal optic nerve, brain stem, etc. Depending on the desired implementation, structure data 522 may identify multiple targets and OARs of any suitable shapes and sizes.

In practice, base training data 521-522 may be user-generated through observations and experience to facilitate supervised learning. For example, base training data 521-522 may be extracted from past treatment plans developed for past patients. Base training data 521-522 may be pre-processed using any suitable data augmentation approach (e.g., rotation, flipping, translation, scaling, noise addition, cropping, any combination thereof, etc.) to produce a new dataset with modified properties to improve model generalization using ground truth. In practice, a 3D volume of the patient that will be subjected to radiation is known as a treatment volume, which may be divided into multiple smaller volume-pixels (voxels). In this case, structure data 522 may specify a class label (e.g., "target," "OAR," etc.) associated with each voxel in the 3D volume.

Any segmentation rule(s) or guideline(s) may be used. For example, rule=R1 may specify a margin around an organ to be contoured. More advanced rule(s) may be used, such as segmentation of a particular structure at an anatomical site, selection of the cutting plane of a structure (e.g., spinal cord), application of different margins at different sides of an organ (e.g., more margin inferior than superior sides of an organ, etc. The segmentation rule(s) may be fine-tuned during subsequent training phase 502 to achieve a more desired classification outcome. As such, base engine 510 represents a pre-trained model that may not be exactly related to the desired classification outcome, but is useful as a starting point for training phase 502. The anatomical site=X associated with base engine 510 may be generic for medical image data, or specific to a particular treatment.

Any suitable deep learning model(s) may be used. For example in FIG. 5, base engine 510 includes multiple (N>1) processing blocks or layers that are each labelled as $B_i$, where i=1, . . . , N (see 511-51N). In this case, pre-training phase 501 may involve finding base weight data (denoted as $wB_i$) that minimizes the training error between training structure data 522, and estimated structure data (not shown for simplicity) generated by base engine 510. The training process is guided by estimating losses associated with the classification error. A simple example of a loss function would be mean squared error between true and predicted outcome, but the loss function could have more complex formulas (e.g., dice loss, jaccard loss, focal loss, etc.). This loss can be estimated from the output of the model, or from any discrete point within the model.

Base weight data $wB_i$ for the $i^{th}$ base layer may be a scalar or multi-dimensional vector. In the case of convolutional neural networks, the $i^{th}$ base layer ($B_i$) may be a convolutional layer that is configured to extract feature data ($F_i$) from training data 520 or the output of the $(i-1)^{th}$ base layer ($B_{i-1}$) using convolution operations. Alternatively and/or additionally, each $i^{th}$ base layer may be configured to perform other operation(s) relating to activation functions, dropout, concatenations, batch normalizations, etc. For example, the first base layer ($B_1$) processes input image data 521 to generate first feature data ($F_1$). The second base layer ($B_2$) processes first feature data ($B_1$) to generate second feature data ($F_2$), and so on. Feature extraction at the $i^{th}$ base layer ($B_i$) may involve applying convolutional filter(s) or kernel(s) to overlapping sites of its input to learn corresponding base weight data $wB_i$.

The feature data ($F_i$) generated by the $i^{th}$ base layer may include a 2D feature map for 2D image data, or a 3D feature map for 3D image data. Feature data ($F_i$) may specify any suitable anatomical feature(s), such as borders, distance to centroid, distance to midline, distance to skin, distance from bone, laterality, presence of vertical and/or horizontal lines, shape-related parameter(s), texture types, any combination thereof, etc. This automatic feature extraction approach should be distinguished from conventional approaches that rely on hand-designed features.

(b) Target Engines (Site=X, Rule R2)

During training phase 502, target engine 540/550 associated with (site=X, rule R2) may be generated based on base engine 510 associated with (site=X, rule R1) and target training data 530. Compared to base training data 520 used during pre-training phase 501, target training data 530 is also associated with site=X, but includes examples relating to rule=R2 instead of R1. For example, rule=R1 may include a general segmentation margin of 2 mm, but the margin is increased to 5 mm according to rule=R2. See also related 420 in FIG. 4.

In practice, even when trained with more limited target training data 530 compared to base training data 520, base engine 510 facilitates faster convergence of target engine 540/550, thereby improving efficiency. Training phase 501 may involve finding target weight data (denoted as $wT_j$, where j=1, ..., M) that minimizes the training error between training structure data 532, and estimated structure data (not shown for simplicity) generated by target engine 540/550. Two example target engines 540-550 will be discussed below.

In a first example (related to 220 in FIG. 2), base engine 510 may be modified (e.g., further trained or fine-tuned) to generate target engine 540. This may involve configuring M≤N base layers (see 511-51M) of base engine 510 to be "variable" such that they may be further trained to generate respective target layers (see 541-54M) of target engine 540. The modification may involve modifying base weight data $wB_i$ (i=1, ..., M) associated with respective base layers 511-51M to obtain corresponding target weight data $wT_j$ (j=1, ..., M). Once training is completed (see 533), each modified base layer ($B_i$) of base engine 510 serves as a corresponding target layer ($T_j$) of target engine 540. During an inference phase (to be discussed using FIG. 8), target engine 550 may be used to perform automatic segmentation.

In a second example (related to 230 in FIG. 2), instead of modifying base engine 510, target engine 550 is built on top of base engine 510. In this case, K≤N base layers (see 511-51K) of base engine 510 may be configured to be "invariable" (i.e., fixed or frozen). This way, the K invariable base layers may be used to generate feature data ($F_K$) based on target training data 530. As indicated at 560 in FIG. 5, the feature data ($F_K$) generated by the $K^{th}$ base layer is then fed into target engine 550 to achieve the desired classification outcome, i.e., automatic segmentation for anatomical site=X according to rule=R2. Target engine 550 may include any suitable number (M) of target layers (see 551-55M). During an inference phase (to be discussed using FIG. 8), both base engine 510 and target engine 550 may be used in sequence to perform automatic segmentation.

In a third example (not shown in FIG. 4 for simplicity), a combination of variable and invariable base layers may be configured (related to 240 in FIG. 2). In this case, base engine 510 may be configured to include K≤N invariable base layers, and at most N–K variable base layers. During training phase 502, the K invariable base layers are fixed and used to process training data 530 to generate feature data ($F_1, ..., F_K$). The feature data then serves as input to modify the variable base layers, and generate any subsequent target layers.

(c) Target Engines (Site=Y, Rule R1 or R3)

Referring now to in FIG. 6, target engines associated with a different anatomical site and/or rule may be generated based on base engine 610. Similar to the example in FIG. 5, base engine 610 may be trained to perform automatic segmentation using base training data 620 associated with (site=X, rule R1). The aim of pre-training phase 601 is to train base engine 610 to map input=image data 621 to output=structure data 622.

In a first example, base engine 610 may be modified to generate first target engine 640 to perform automatic segmentation for a different target anatomical site=Y according to target rule=R1. For example, X may represent the bladder region, and Y the lung region. In another example, one could obtain base engine 510/610 that is trained to perform base task=breast segmentation and train it further to generate a target engine to perform target task=breast and lymph node segmentation using example contours that include both the breast and lymph nodes.

This way, knowledge relating to structure(s) in base anatomical site=X may be transferred from base engine 610 to target engine 640 for automatic segmentation in target anatomical site=Y. During training phase 602, M≤N variable base layers (see 611-61M) of base engine 610 may be modified to generate respective target layers (see 641-64M). The modification may involve modifying base weight data $wB_i$ (i=1, ..., M) associated with respective base layers 611-61M to obtain corresponding target weight data $wT_j$ (j=1, ..., M). Once training is completed (see 633), each modified base layer ($B_i$) of base engine 610 serves as a corresponding target layer ($T_j$) of target engine 640.

In a second example, a combination of invariable and variable base layers may be configured to generate second target engine 650 to perform automatic segmentation for target anatomical site=Y according to a different target rule=R3. For simplicity, consider four base layers 611-614 that have been repurposed for target engine 650. Invariable base layers (see 611-612) are fixed and used to generate feature data (e.g., $F_1$ and $F_2$) based on target training data 630. The remaining variable base layers are modified based on the feature data to generate respective target layers 651-652. Feature data from the variable base layers (e.g., $F_3$ and $F_4$) is then used to train additional target layers 653-65M. In practice, it should be understood that any suitable number of invariable and variable base layers may be configured.

In practice, training process 502/602 may include the validation of target engines 540-550 in FIG. 5 and 640-650 in FIG. 6 using any suitable approach. For example, quality metrics may be tracked for validation purposes, such as dice score, average surface distance (measuring the error of the contoured surface location relative to the ground truth), etc.

Dose Prediction and Other Planning Tasks

Figure 7:
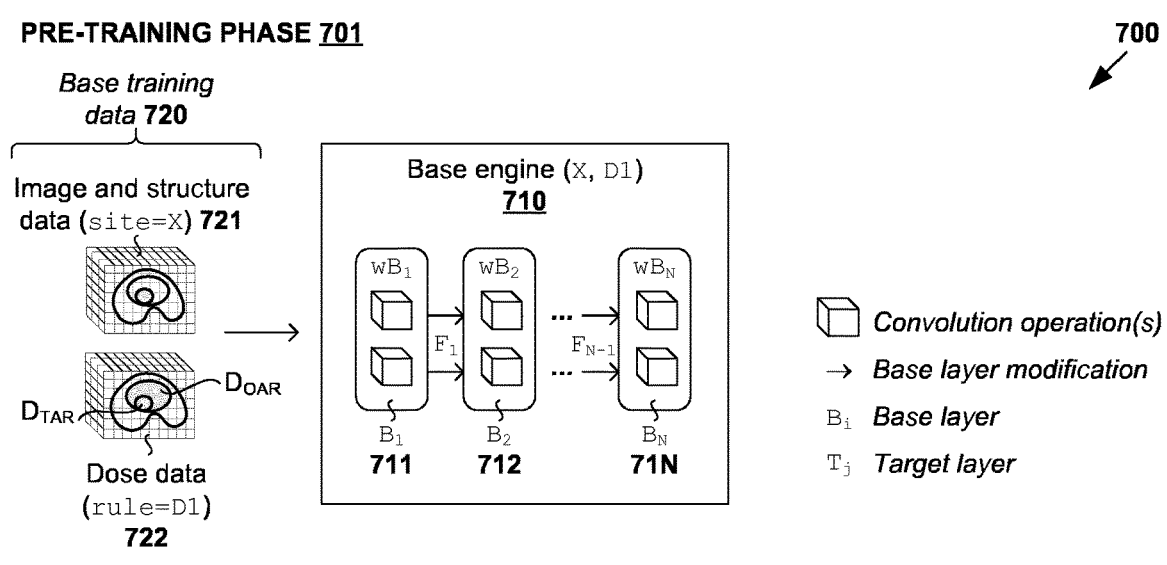
FIG. 7 is a schematic diagram illustrating example deep transfer learning for dose prediction.

FIG. 7 is a schematic diagram illustrating example deep transfer learning 700 for dose prediction. During pre-training phase 701, base engine 710 may be trained using any suitable base training data 720 to perform dose prediction for anatomical site=X according to prediction rule=D1. The aim is to train base engine 710 to map example input data=image data and structure data 721 (i.e., segmented image data), and example output data=dose data 722. Any suitable constraint(s) may be used, such as limiting dose prediction to the vicinity of target(s) or certain dose levels only.

Dose data 722 (e.g., 3D dose data) may specify dose distributions for a target (denoted "$D_{TAR}$") and an OAR (denoted "$D_{OAR}$"). For example, in relation to prostate cancer, dose data 712 may specify dose distributions for a target representing the patient's prostate, and an OAR representing a proximal healthy structure such as rectum or bladder. In practice, dose data 722 may specify the dose distributions for the whole 3D volume, not just the target and OAR volumes. Depending on the desired implementation, dose data 722 may include spatial biological effect data (e.g., fractionation corrected dose) and/or cover only part of the treatment volume. Besides structure data 721, additional input data may include beam geometry data associated with the treatment delivery system.

During training phase 702, knowledge learned by base engine 710 may be transferred to target engines 740-750. In a first example, target engine 740 associated with anatomical site=X according to rule=D2 is generated. This involves modifying variable base layers 711-71M of base engine 710 based on target training data 730-732 to generate respective target layers 741-74M. In a second example, target engine 750 associated with anatomical site=Y according to rule=D1 is generated. In particular, based on target training data 733-735, invariable base layers 711-71K of base engine 710 may be used to generate feature data (see 760) to train target layers 751-75M.

In practice, any suitable prediction rules D1 and D2 may be used, such as rules relating to organ sparing, target coverage (and dose prescription), and normal tissue dose. Additionally or alternatively, the prediction rule(s) may relate to treatment techniques (e.g., IMRT, VMAT, etc.), cancer type, machine specification (e.g., energy and field shape, clinical practices for field placements, etc. All these will have an impact on the predicted dose data. The prediction rule(s) may be learned implicitly from training data 720/730/733, or optionally provided as input parameters for certain types of deep learning engines.

Besides automatic segmentation in FIGS. 5-6 and dose prediction in FIG. 7, deep transfer learning may be implemented for other radiotherapy treatment planning tasks, such as treatment delivery data estimation, treatment outcome prediction, etc. In relation to treatment delivery data estimation, the estimated treatment delivery data (i.e., output data) may include structure projection data, fluence map data, etc. For example, a target engine may be trained to perform structure projection data, such as based on image data, structure data, dose data, or any combination thereof. The structure projection data may include data relating to beam orientations and machine trajectories for a treatment delivery system (see 160 in FIG. 1 and FIG. 16).

In another example, a target engine may be trained to perform fluence map estimation, such as 2D fluence maps for a set of beam orientations/trajectories, machine control point data (e.g., jaw and leaf positions, gantry and couch positions), etc. Fluence maps will be explained further using FIG. 10. Any additional and/or alternative training data may be used, such as field geometry data, monitor units (amount of radiation counted by machine), quality of plan estimate (acceptable or not), daily dose prescription (output), field size or other machine parameters, couch positions parameters or isocenter position within patient, treatment strategy (use movement control mechanism or not, boost or no boost), treat or no treat decision.

Although exemplified using deep convolutional neural networks, it should be understood that any alternative and/or additional deep learning model(s) may be used to implement the base and target engines. For example, base engines and target engines described in the present disclosure may include multiple processing pathways described in related U.S. patent application Ser. No. 16/145,461. The processing pathways may be configured to process input data (e.g., image data) at different resolution levels. This way, a larger receptive field may be achieved.

In practice, medical image data generally includes both local and global feature data of a patient's anatomy, where the terms "local" and "global" are relative in nature. For example, the local feature data may provide a microscopic view of the patient's anatomy, such as tissue texture, whether a structure has a limiting border, etc. In contrast, the global feature data may provide a relatively macroscopic view of the patient's anatomy, such as which region the anatomy is located (e.g., prostate, etc.), orientation (e.g., to the left, to the right, front, back), etc.

Inference Phase

Figure 8:
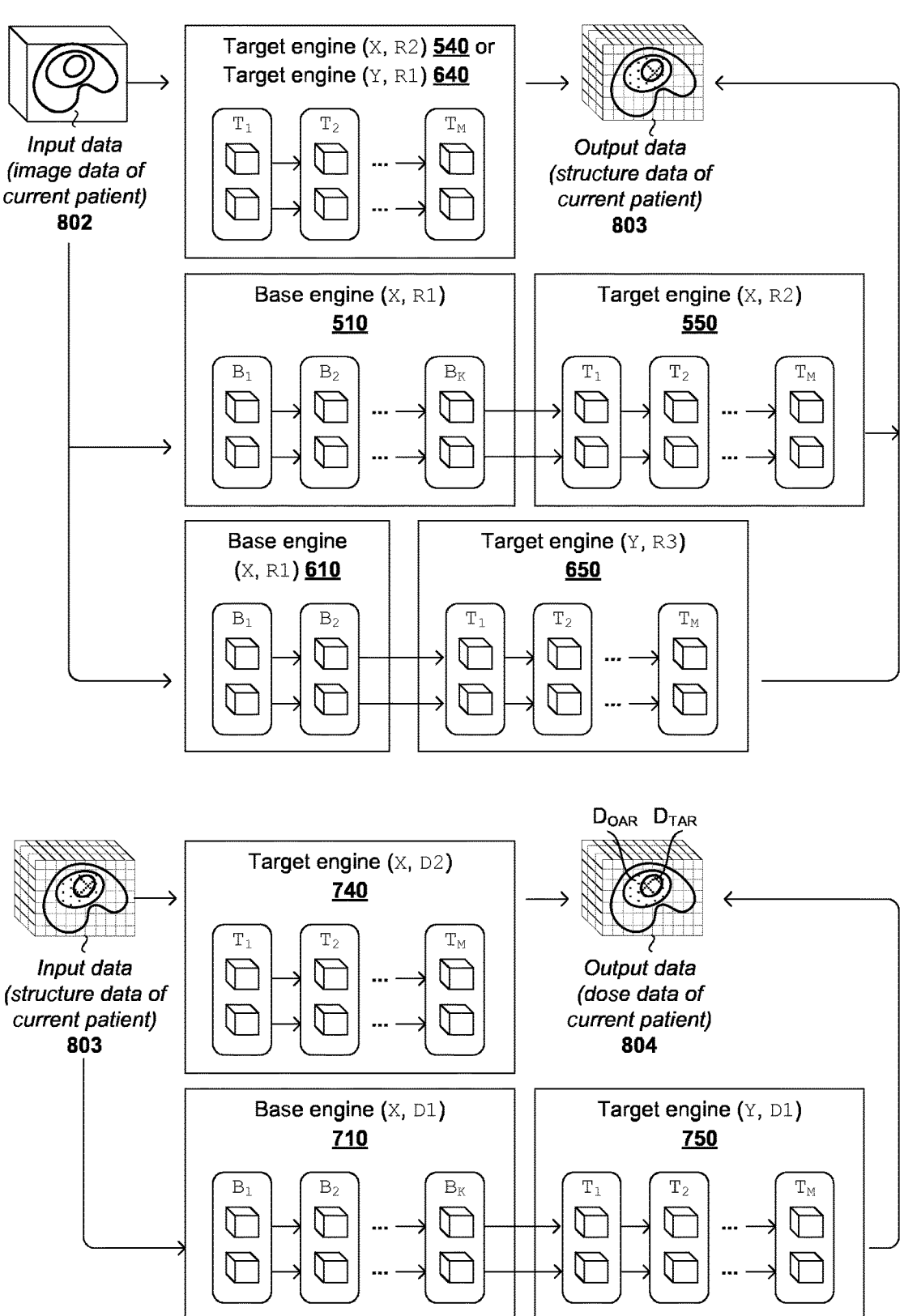
FIG. 8 is a schematic diagram illustrating an example inference phase for target engines generated according to the examples in FIG. 5, FIG. 6 and FIG. 7.

FIG. 8 is a schematic diagram illustrating example inference phase 801 for target engines generated according to the examples in FIG. 5, FIG. 6 and FIG. 7. Once trained, target engine 540/550/640/650 may be used by a clinician during inference phase 801 to perform automatic segmentation to generate output data=patient structure data 803 based on input data=image data 802 of a current patient. In one example, image data 802 is processed using target layers of target engine 540/640 generated by modifying variable base layers of base engine 510/610. In another example, image data 802 is processed by both base engine 510/610 and target engine 550/650 arranged in a sequence. In practice, it should be noted that the "current patient" is one of multiple patients who are being processed at the same time during inference phase 801. Also, automatic segmentation may be performed when image data 802 is captured and being transferred to a storage system (e.g., picture archiving and communication system (PACS, etc.).

Similarly, target engine 640/650 may be used by a clinician during inference phase 801 to perform automatic segmentation to generate output data=dose data 804 of a current patient based on input data=image data and structure data 803 associated with the patient. In one example, input data 803 is processed using target layers of target engine 740 generated by modifying variable base layers of base engine 510/610. In another example, input data 803 is processed by both base engine 710 and target engine 750 arranged in a sequence. As discussed using FIG. 7, any additional and/or alternative input data and output data may be used. During radiotherapy treatment planning, a treatment plan may be generated based on structure data 803 and dose data 804 generated during inference phase 801 in FIG. 8.

Figure 9:
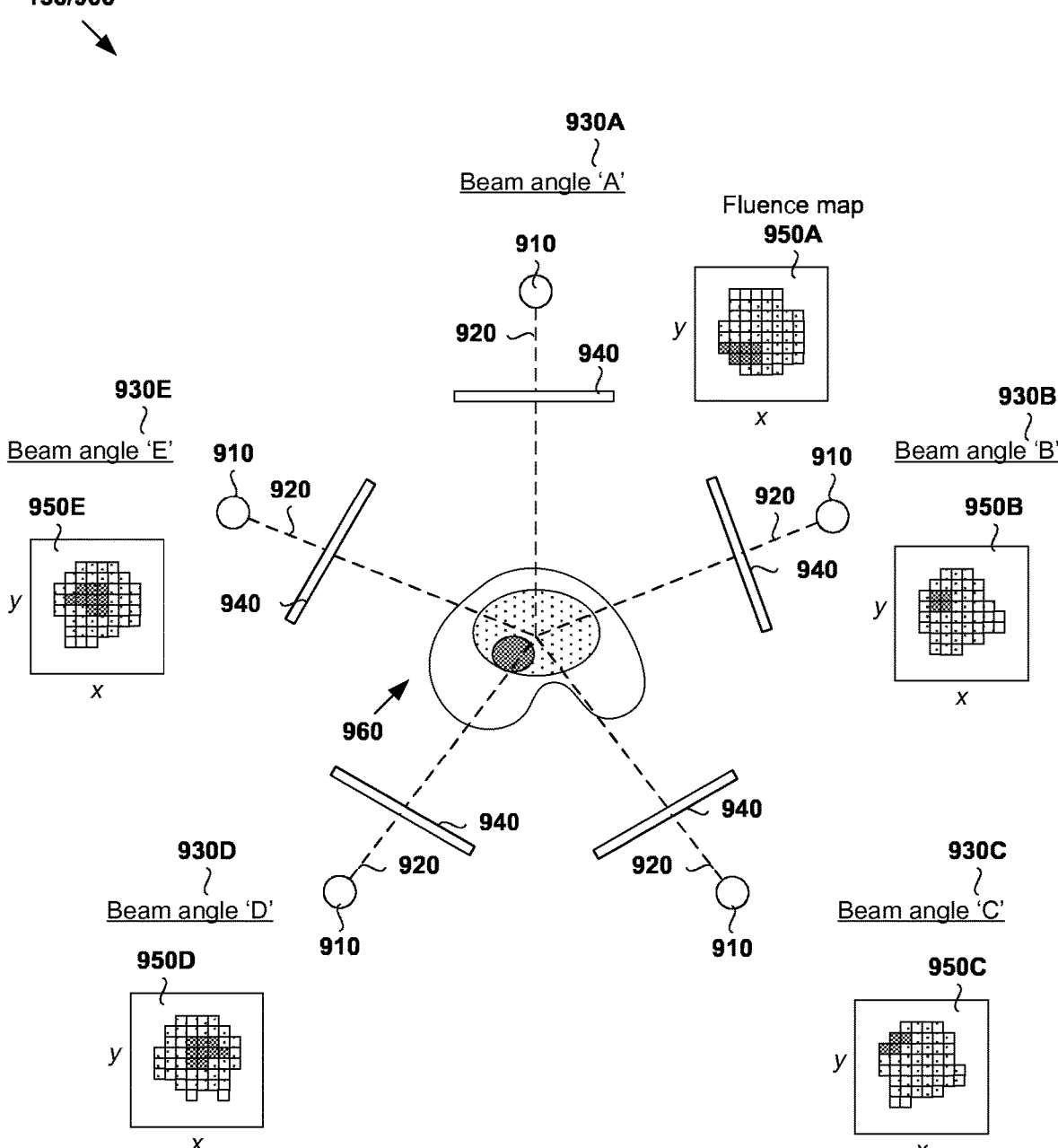
FIG. 9 is a schematic diagram of an example treatment plan generated or improved based on output data in the examples in FIG. 8.

FIG. 9 is a schematic diagram of example treatment plan 156/900 generated or improved based on output data in the examples in FIG. 8. Treatment plan 156 may be delivered using any suitable treatment delivery system that includes radiation source 910 to project radiation beam 920 onto treatment volume 960 representing the patient's anatomy at various beam angles 930.

Although not shown in FIG. 9 for simplicity, radiation source 910 may include a linear accelerator to accelerate radiation beam 920 and a collimator (e.g., MLC) to modify or modulate radiation beam 920. In another example, radiation beam 920 may be modulated by scanning it across a target patient in a specific pattern with various energies and dwell times (e.g., as in proton therapy). A controller (e.g., computer system) may be used to control the operation of radiation source 920 according to treatment plan 156.

During treatment delivery, radiation source 910 may be rotatable using a gantry around a patient, or the patient may be rotated (as in some proton radiotherapy solutions) to emit radiation beam 920 at various beam orientations or angles relative to the patient. For example, five equally-spaced beam angles 930A-E (also labelled "A," "B," "C," "D" and "E") may be selected using a deep learning engine configured to perform treatment delivery data estimation. In practice, any suitable number of beam and/or table or chair angles 930 (e.g., five, seven, etc.) may be selected. At each beam angle, radiation beam 920 is associated with fluence plane 940 (also known as an intersection plane) situated outside the patient envelope along a beam axis extending from radiation source 910 to treatment volume 960. As shown in FIG. 9, fluence plane 940 is generally at a known distance from the isocenter.

Example Planning System

Examples of the present disclosure may be deployed in any suitable manner, such as a standalone system, web-based planning-as-a-service (PaaS) system, etc. In the following, an example planning system (also known as a "computer system") will be described using FIG. 10, which is a schematic diagram illustrating example network environment 1000 in which deep transfer learning for radiotherapy treatment planning may be implemented. Depending on the desired implementation, network environment 1000 may include additional and/or alternative components than that shown in FIG. 10.

Figure 10:
FIG. 10 is schematic diagram illustrating an example network environment in which deep transfer learning for radiotherapy treatment planning may be implemented.

In the example in FIG. 10, network environment 1000 includes planning system 1010 that is accessible by multiple user devices 1001-1003 via any suitable physical network (e.g., local area network, wide area network, etc.) In practice, user devices 1001-1003 may be operated by various users located at a particular clinical site, or different clinical sites. Planning system 1010 may be implemented using a multi-tier architecture that includes web-based user interface (UI) tier 1011 to interact with user devices 1001-1003; training infrastructure 1012 (also known as an application tier) to perform deep transfer learning; and data tier 1013 to facilitate data access to and from datastore 1020. Depending on the desired implementation, planning system 1010 may be deployed in a cloud computing environment, in which case multiple virtualized computing instances (e.g., virtual machines, containers) may be configured to implement various functionalities of tiers 1011-1013. The cloud computing environment may be supported by on premise cloud infrastructure, public cloud infrastructure, or a combination of both.

In more detail, UI tier 1011 may be configured to provide any suitable interface(s) to interact with user devices 1001-1003, such as graphical user interface (GUI), command-line interface (CLI), application programming interface (API) calls, any combination thereof, etc. Training infrastructure may be configured to perform train base engines during a pre-training phase, and deep transfer learning (i.e., model adaptation) to generate target engines during a training and validation phase.

Data tier 1013 may be configured to facilitate access (by UI tier 1011 and training infrastructure 1012) to multiple base and target engines stored in datastore 1020. Using the examples discussed using FIGS. 5-7, datastore 1020 may store base engine 510/610 associated with (site=X, segmentation rule=R1), and base engine 710 associated with (site=X, dose prediction rule=D1). This way, it is not necessary for user devices 1001-1003 to interact with backend training infrastructure 1012 and data tier 1013 directly, thereby providing abstraction and enhancing security.

(a) Pre-Training Phase

FIG. 11 is a flowchart of an example process for deep transfer learning for radiotherapy treatment planning using example planning system in FIG. 10. Example process 1100 may include one or more operations, functions, or actions illustrated by one or more blocks, such as 1105 to 1180. The various blocks may be combined into fewer blocks, divided into additional blocks, and/or eliminated based upon the desired implementation. Example process 1100 may be implemented using any suitable computer system(s), an example of which will be discussed using FIG. 16.

At 1105 in FIG. 11, during a pre-training phase, multiple base engines may be trained to perform respective base tasks using base training data. Each base engine may be trained to perform a particular base task associated with a particular site (e.g., site X=bladder region) according to a particular rule (e.g., R1=segmentation margin of 2 mm). Each base engine may be trained to perform any suitable base task, such as segmentation (see FIGS. 5-6), dose prediction (see FIG. 7), treatment delivery data estimation, treatment outcome prediction, etc. Once pre-training is performed, multiple base engines (see 1021-1022) may be stored in datastore 1020 for later access during training phase. Depending on the desired implementation, block 1105 may be performed by training infrastructure 1012 (as shown in FIG. 11), user device 1001/1002/1003, an alternative system, or any combination thereof.

(b) Example User Interfaces

At 1110 in FIG. 11, planning system 1010 may provide first UI(s) supported by UI tier 1011 for a user to send a request to generate a target engine to perform a target task. At 1120, the user may interact with the first UI(s) to send a request to generate the target engine based on a base engine and target training data. The request may be generated using an interface (e.g., GUI, API, CLI) supported by UI tier 1011. For example in FIG. 10, first user device 1001 may send a first request (see 1031) to UI tier 1011 by interacting with a GUI. Second user device 1002 may send a second request (see 1032) by invoking API call(s), and third user device 1003 may send a third request (see 1033) using CLI command(s).

Some example UI(s) will be explained using FIGS. 12A-B and 13A-B, each being a schematic diagram illustrating example interface 1200 for target engine generation during training phase. To facilitate deep transfer learning, requests 1031-1033 may each include any suitable target training data (see 1121 in FIG. 11 and FIG. 12A). Requests 1031-1033 may include any additional data for generating respective target engines, such as base engine selection parameter data (see 1122 in FIG. 11 and FIG. 12B), training parameter data (see 1123 and FIG. 13A), validation parameter data (see 1124 and FIG. 13B), etc. In practice, training interface 1200 may include any suitable "UI elements" with which a user may interact, such as windows, panes, buttons, menus, text boxes, tabs, lists, application icons, menu bars, scroll bars, title bars, status bars, toolbars, dropdown lists, any combination thereof, etc.

At 1210 in FIG. 12A (see "Target Engine" view), training interface 1200 includes UI elements for a user to provide target training data associated with multiple past patients, or specify a link (e.g., a uniform resource locator (URL), network path, etc.) to the target training data. The target training data may include image data in any suitable format capable of being processed by training infrastructure 1012, such as Digital Imaging and Communications in Medicine (DICOM) images. Using the automated segmentation example in FIG. 5, first request 1031 may include target training data 530 to generate target engine 540/550 associated with (site=X, target rule=R2). Second request 1032 may include target training data 630 in FIG. 6 to generate target engine 640/650 associated with (site=Y, target rule=R1). For dose prediction in FIG. 7, third request 1033 may include target training data 730 to generate target engine 740/750 associated with (site=X, target rule=D2).

At 1220 in FIG. 12B (see "Base Engine" view), training interface 1200 includes UI element(s) for a user to specify selection parameter data for selecting a base engine. On a left pane (see 1222) of training interface 1200, base engines may be searched or filtered based on task type (e.g., segmentation, dose prediction), anatomical site, structure, base engine provider (e.g., providers P1 and P2), performance metric, keyword(s), etc. On a right pane (see 1224), a list of matching base engines are presented for selection, such as ID, anatomical site, base rule (e.g., segmentation margin=R1, dose prediction rule=D1), structure(s), performance metric(s), etc. In practice, a user may first select a planning task and a general anatomical site, before specifying more specific requirements. In response to receiving the base engine selection parameter data, UI tier 1011 may retrieve a list of candidate base engines and present the list on interface 1200 in FIG. 12B for user's selection.

At 1226 in FIG. 12B, training interface 1200 includes UI element(s) for a user to specify mapping data for use during the training phase. Based on the mapping data, training infrastructure 1012 may map a target name (or target ID) associated with the target engine with a corresponding base name (or base ID) associated with a base engine. For example, a base engine for automated segmentation may provide a list of structures as its output. The structures may be referred to as "Breast Left," "Breast Right," and "Heart" by the base engine. In the target training data provided by the user, however, different (target) names may be used for the same structures, such as "Brust Links," "Brust Rechts" and "Herz" (in German), or "BR-L," "BR-R" and "H" (in shorthand specific to a clinical site). In this case, the mapping data may be provided to training architecture 1012 to translate a base name (e.g., "Breast Right" with ID=112) to its corresponding target name (e.g., "BR-R" with ID=131). Where possible, the mapping may also be automatically handled by planning system 1010 through base/target structure ID mapping. The mapping may also be based on structure IDs from any suitable clinical standards or reference ontology, such as the Foundational Model of Anatomy (FMA) Ontology, etc.

At 1310 in FIG. 13A (see "Training" view), training interface 1200 further includes UI element(s) for a user to configure training parameter data to guide training infrastructure 1012 during training phase. Under "base layer configuration" (see 1312), a base engine may be configured to include variable base layer(s) and/or invariable base layer(s). Depending on the desired implementation, the number (or percentage) of variable and invariable base layers may be configured. Under "training hyperparameters" (see 1314), hyperparameters associated with deep transfer learning may be configured, such as dropout rate, activation function, number of training epochs, learning rate, number of hidden units, convolution kernel width, etc. In practice, configuration of base layers and training parameters may be performed automatically by training infrastructure 1012 instead of relying on a user's input. Depending on the training hyperparameters changed, a full retraining may be required due to changes in an underlying graph associated with the base engine. For example, a full retraining may be required in response to changes to hyperparameters such as convolutional kernel width or activation function. However, a full retraining is generally not required when parameters such as loss functions, learning rates and number of epochs are updated.

At 1320 in FIG. 13B (see "Validation" view), training interface 1200 further includes UI element(s) for a user to configure validation parameter data to guide training infrastructure 1012 during validation phase. Under "validation criteria" (see 1332), for example, thresholds for validation parameter data may be configured, such as dice score, average surface difference, Hausdorff distance, etc. Although discussed using FIGS. 12A-B and 13A-B, it should be understood that request 1032/1033 generated using API/CLI may similarly include target training data, base engine selection data, training parameter data, validation parameter data, or any combination thereof.

(b) Training Phase

Referring to FIG. 11, at 1125, planning system 1010 (e.g., UI tier 1011) detects a request (e.g., 1031) from a user device (e.g., 1001) to generate a target engine. At 1130 in FIG. 11, in response to detecting the request, planning system 1010 (e.g., training infrastructure 1012) may select a base engine from multiple base engines that have been pre-trained at block 1105. The selection at block 1130 may be based on manual selection by the user, or automatic selection by training infrastructure 1012. In the case of manual selection, the request may specify (e.g., using model or engine ID) a particular base engine selected by the user, such as using training interface 1200 in FIG. 12B. In the case of automatic selection, the request may specify selection parameter data for training infrastructure 1012 to select the base engine automatically, such as an anatomical site, structure(s) or organ(s), performance metric(s), base engine provider, or any combination thereof.

At 1135 in FIG. 11, training infrastructure 1012 configures the base engine selected at block 1130 to include variable base layer(s), invariable base layer(s), or a combination of both. Block 1135 may be performed based on the base layer configuration (see 1312 in FIG. 13A) specified in a request, or default settings (where applicable). At 1140 in FIG. 11, training infrastructure 1012 performs deep transfer learning to generate a target engine based on the base engine selected at block 1130. During the training phase, deep transfer learning may be performed based on mapping data (see FIG. 12B) and/or training parameter data (see FIG. 13A), etc. In practice, the base engine at block 1135 may be represented using a set of weights (i.e., variable or invariable depending on their configuration) that will be used as a starting point for generating the target engine.

In a first example, a base engine (e.g., 510 in FIG. 5 and 610 in FIG. 6) may be configured to include M≤N variable base layers. In this case, training infrastructure 1012 may generate multiple target layers of the target engine (e.g., 540 in FIG. 5 and 640 in FIG. 6) by modifying the variable base layers based on target training data (e.g., 530 in FIG. 5 and 630 in FIG. 6). See 740 in FIG. 7.

In a second example, a base engine (e.g., 510 in FIG. 5) may be configured to include K≤N invariable base layers, which are not modified during training. In this case, training infrastructure 1012 may generate multiple target layers of the target engine (e.g., 550 in FIG. 5) based on feature data that is generated by the invariable base layers based on the target training data (e.g., 530 in FIG. 5). See 750 in FIG. 7.

In a third example, a base engine (e.g., 610 in FIG. 6) may be configured to include a combination of variable and invariable base layers. In this case, training infrastructure 1012 may generate multiple target layers of the target engine (e.g., 650 in FIG. 6) by generating feature data using the invariable base layers (see 611-612) based on the target training data. The remaining variable base layers are then modified based on the feature data to generate additional target layers.

Examples of deep transfer learning explained using FIGS. 1-9 are applicable here, and will not be repeated in detail for brevity. In practice, the user's request may cause training infrastructure 1012 to (a) train the target engine to meet specific requirements, or (b) tune a base engine to better match different features present in a particular patient population. For case (a), the request may specify guidelines such as additional margins, selection of the cutting plane of long organs (e.g., spinal cord), etc.

For case (b), retraining might be required if the anatomy of the patient population differs from the patient population used to train the original model (i.e., base engine). The differences in the patient population may include differences in body mass index and size, or even the shape of contoured organs (e.g., the breast size might differ between different geographies due to differences in the amount of fat tissue). The differences may be associated with the anatomical site, such as when a base engine developed for intact breasts may be retrained for patients with one breast removed. The base and target engines may be based on any suitable medical imaging modality, such as CT, CBCT, PET, MRI, or any combination thereof, etc.

(d) Validation Phase

At 1145 in FIG. 11, training infrastructure 1012 performs validation of the target engine, such as based on validation parameter data configured using training interface 1200 in FIG. 13B. Validation may be performed to improve results, such as to prevent overfitting or falling into a local minimum, provide an indication of convergence, etc. In practice, the target training data provided by the user may be divided into a training set for the training phase, and a validation set for the validation phase.

In response to determination a particular iteration of the target engine does not satisfy certain validation criteria, the training phase continues at block 1140 at the next iteration. Otherwise, at 1150, a response (e.g., 1041/1042/1043 in FIG. 10) is sent to the user device (e.g., 1001/1002/1003) to facilitate access to the generated target engine and any associated data. The generated target engine (e.g., 1023/1024 in FIG. 10) may be stored in datastore 1020.

Figure 14A:
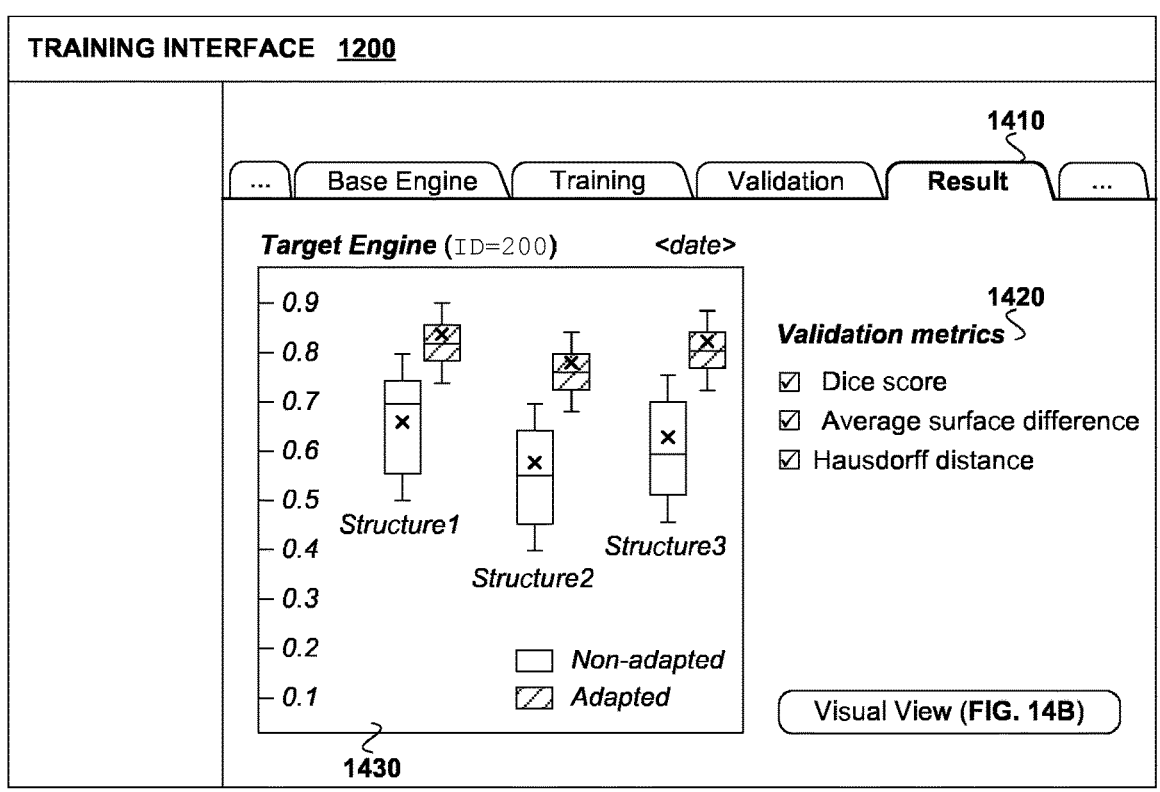
FIG. 14A is schematic diagram illustrating a first example interface for target engine generation during validation phase.
Figure 14B:
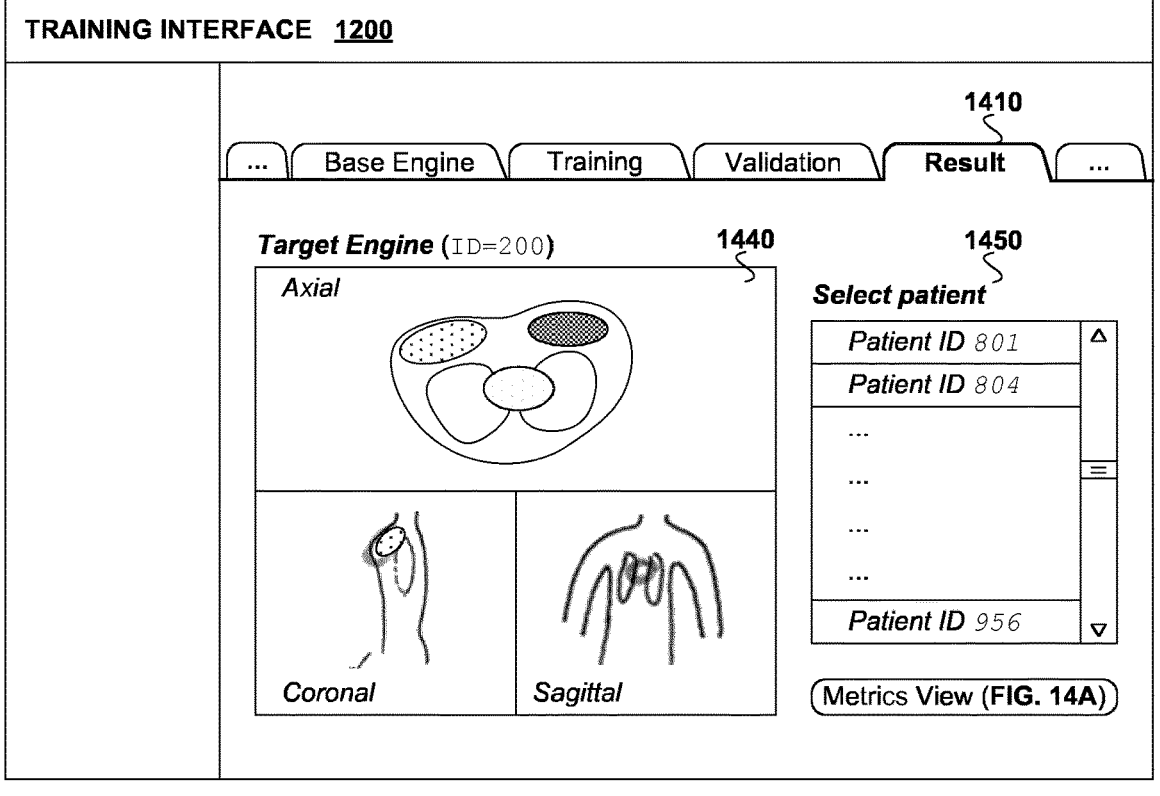
FIG. 14B is schematic diagram illustrating a second example interface for target engine generation during validation phase.

Planning system 1010 may generate statistics and visual inspection on how well the target engine has been adapted from the base engine. Some examples are shown in FIGS. 14A-B (see "Result" view at 1410), which are each a schematic diagram illustrating training interface 1200 for target engine generation during validation phase. At 1420 and 1430 in FIG. 14A, a validation metrics view of training interface 1200 may present statistics or metrics associated with the generated target engine (e.g., ID=200). Example metrics include dice scores (or slice-wise dice scores), accuracy, sensitivity, average surface difference, Hausdorff distance, etc.

As a reference, the quality statistics could be provided also from applying the target engine on a larger set of target training data that the base engine was trained with. In practice, the validation criteria may be specific to a particular application, target task, anatomical site, etc. For large structures, for example, one typically gets higher dice scores compared to smaller structures. These scores may be used for tracking whether the target engine improves or not. In the example in FIG. 14A, it is desirable to have the "adapted" (target) models performs better than the "non-adapted" (base) models. Depending on the desired implementation, training interface 1200 may provide a UI that presents a how the target engine performs on the "base" validation cases (i.e., used for validating the base engine) and any additional validation cases (i.e., used for validating the target engine). This way, the user may distinguish between a decrease in generalizability and an increase in site-specific performance.

At 1440 in FIG. 14B, a visual inspection view of training interface 1200 may present how well the target engine has been adapted. For example, a specific patient may be selected (see 1450) to compare the ground truth against the output of the target engine for that patient. The visual inspection may be presented in multiple anatomical planes, including the transverse or axial plane, sagittal plane and coronal plane. The axial plane is parallel to the ground and divides the body into top and bottom parts. The sagittal or lateral plane divides the body into left and right halves. The coronal or frontal plane divides the body into front and back sections.

(e) Inference Phase

After the training phase, the generated target engine may be provided to the user for local application or for cloud-based planning application. At 1155-1160 in FIG. 11, UI tier 1011 is further configured to provide a planning interface for a user (e.g., clinician) to interact with. At 1165, through the interaction with the planning interface, the user may access and instruct a target engine to perform a target task for an individual patient. At 1170-1180, planning system 1010 performs the target task (e.g., automated segmentation) for the individual patient and responds to any suitable output data (e.g., structure data) and statistics, which will be accessible via interface(s) supported by UI tier 1011.

Figure 15A:
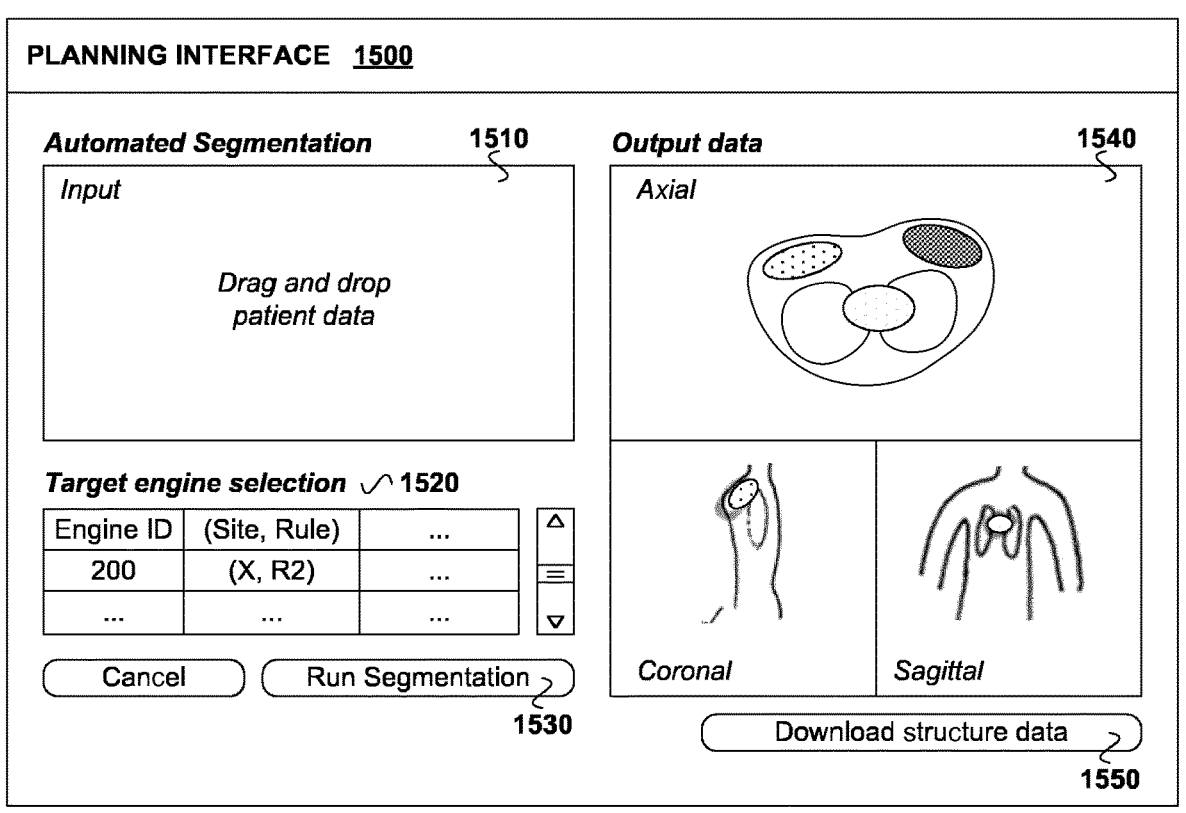
FIG. 15A is schematic diagram illustrating an example planning interface for automated segmentation during inference phase.

A first example is shown in FIG. 15A, which is a schematic diagram illustrating planning interface 1500 for automated segmentation during inference phase. Planning interface 1500 includes UI elements for the user to provide input=image data associated with a patient (see 1510); and select and instruct a particular target engine (see 1520) trained to perform automated segmentation (see 1530). For example, target engine 540/550 in FIG. 5 may be selected to perform automated segmentation associated with (site X, rule R2), or target engine 640/650 in FIG. 6 for (site Y, rule R1 or R3). Once automated segmentation is completed, planning interface 1500 includes UI elements to present output=structure data associated with the patient (see 1540), and for the user to download the output structure data (see 1550). In practice, planning interface 1500 may be integrated with any suitable system, such as treatment planning platform(s), patient database(s), etc. One example of the treatment planning platform is the Eclipse™ Treatment Planning Platform (available from Varian Medical Systems), etc.

Figure 15B:
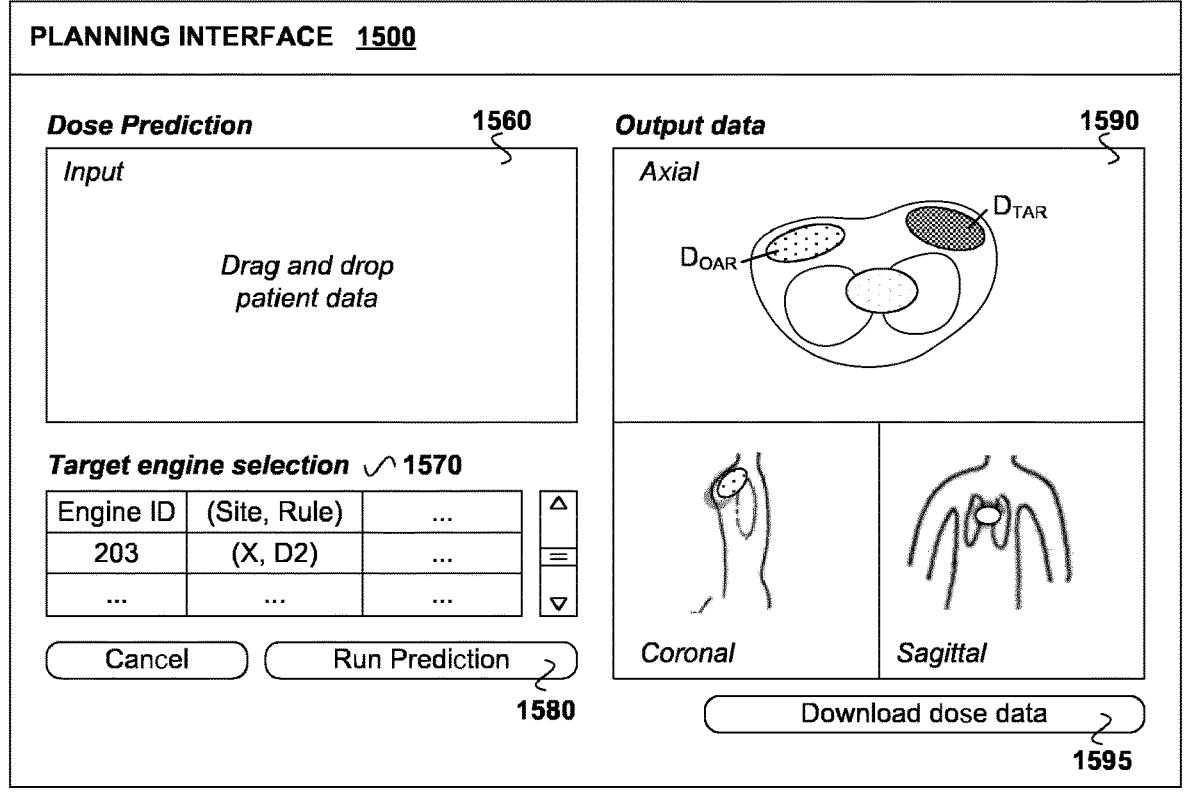
FIG. 15B is schematic diagram illustrating an example planning interface for dose prediction during inference phase.

A second example is shown in FIG. 15B, which is a schematic diagram illustrating planning interface 1500 for dose prediction during inference phase. Planning interface 1500 includes UI elements for the user to provide input=image data and structure data associated with a patient (see 1560); and select and instruct a particular target engine (see 1570) trained to perform dose prediction (see 1580). Using the examples in FIG. 7, target engine 740/750 may be instructed to perform dose prediction associated with (site X, prediction rule D1 or D2). Once dose prediction is completed, planning interface 1500 includes UI elements to present output=dose data associated with the patient (see 1590), and for the user to download the output dose data (see 1595).

Computer System

The above examples can be implemented by hardware, software or firmware or a combination thereof. FIG. 16 is a schematic diagram of example computer system 1600 for deep transfer learning for radiotherapy treatment planning. In this example, computer system 1600 (also known as a treatment planning system) may include processor 1610, computer-readable storage medium 1620, system interface 1640 to interface with radiotherapy treatment delivery system 160, and bus 1630 that facilitates communication among these illustrated components and other components.

Processor 1610 is to perform processes described herein with reference to FIG. 1 to FIG. 15B. Computer-readable storage medium 1620 may store any suitable information 1622, such as information relating to training data, deep learning engines, image data, output data, etc. Computer-readable storage medium 1620 may further store computer-readable instructions 1624 which, in response to execution by processor 1610, cause processor 1610 to perform processes described herein. Treatment may be delivered according to treatment plan 156 using treatment planning system 160 explained using FIG. 1, the description of which will not be repeated here for brevity. In practice, computer system 1600 may be part of a computation cluster that includes multiple computer systems. Computer system 1600 may include any alternative and/or additional component(s), such as graphics processing unit (GPU), message queues for communication, blob storage or databases, load balancer(s), specialized circuits, etc. As discussed using FIG. 10, computer system 1600 may be deployed in any suitable manner, including a service-type deployment in an on-premise cloud infrastructure, public cloud infrastructure, a combination thereof, etc.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. Throughout the present disclosure, the terms "first," "second," "third," etc. do not denote any order of importance, but are rather used to distinguish one element from another.

Those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

Although the present disclosure has been described with reference to specific exemplary embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense.

We claim:

1. A method for a computer system, interfaced with a treatment delivery system, to perform deep transfer learning for radiotherapy treatment planning, wherein the method comprises:

obtaining, by the computer system, a base deep learning engine that is pre-trained to perform a base radiotherapy treatment planning task, wherein the base deep learning engine includes multiple base layers; and based on the base deep learning engine, generating, by the computer system, a target deep learning engine to perform a target radiotherapy treatment planning task by performing at least one of the following, wherein the base deep learning engine is trained based on base training data associated with the base radiotherapy treatment planning task in a first phase, the target deep learning engine is trained based on target training data associated with the target radiotherapy treatment planning task in a second phase later than the first phase, and the target radiotherapy treatment planning task and the base radiotherapy treatment planning task are two different radiotherapy treatment planning tasks:

configuring a variable base layer among the multiple base layers of the base deep learning engine, and generating one of multiple target layers of the target deep learning engine by modifying the variable base layer; and configuring an invariable base layer among the multiple base layers of the base deep learning engine, and generating one of multiple target layers of the target deep learning engine based on feature data generated using the invariable base layer;

performing, by the computer system, the target radiotherapy treatment planning task to generate output data based on input data associated with a particular patient in a third phase using the target deep learning engine, wherein the third phase is later than the second phase; and generating, by the computer system, a treatment plan based on the output data, wherein the treatment delivery system retrieves the treatment plan and delivers a radiotherapy treatment to the particular patient according to the treatment plan.

2. The method of claim 1, wherein generating the target deep learning engine comprises:

based on the base deep learning engine that is pre-trained to perform the base radiotherapy treatment planning task associated with a base anatomical site, generating the target deep learning engine to perform the target radiotherapy treatment planning task associated with a target anatomical site.

3. The method of claim 1, wherein generating the target deep learning engine comprises:

based on the base deep learning engine that is pre-trained to perform the base radiotherapy treatment planning task according to a base rule, generating the target deep learning engine to perform the target radiotherapy treatment planning task associated with a target rule.

4. The method of claim 1, wherein generating the target deep learning engine comprises:

generating the target deep learning engine to perform one of the following target radiotherapy treatment planning tasks: automatic segmentation to generate structure data based on image data; dose prediction to generate dose data based on structure data and image data; and treatment delivery data prediction to generate treatment delivery data.

5. The method of claim 1, wherein generating the target deep learning engine comprises one of the following:

configuring the multiple base layers of the base deep learning engine to be variable base layers; and generating the multiple target layers by modifying the respective variable base layers based on the target training data.

6. The method of claim 1, wherein generating the target deep learning engine comprises:

configuring the multiple base layers of the base deep learning engine to be invariable base layers; and generating the feature data using the invariable base layers based on the target training data.

7. The method of claim 1, wherein generating the target deep learning engine comprises:

configuring the multiple base layers of the base deep learning engine to include both invariable base layers and variable base layers.

8. A non-transitory computer-readable storage medium that includes a set of instructions which, in response to execution by a processor of a computer system, interfaced with a treatment delivery system, cause the processor to perform a method of deep transfer learning for radiotherapy treatment planning, wherein the method comprises:

obtaining, by the computer system, a base deep learning engine that is pre-trained to perform a base radiotherapy treatment planning task, wherein the base deep learning engine includes multiple base layers; and based on the base deep learning engine, generating, by the computer system, a target deep learning engine to perform a target radiotherapy treatment planning task by performing at least one of the following, wherein the base deep learning engine is trained based on base training data associated with the base radiotherapy treatment planning task in a first phase, the target deep learning engine is trained based on target training data associated with the target radiotherapy treatment planning task in a second phase later than the first phase, and the target radiotherapy treatment planning task and the base radiotherapy treatment planning task are two different radiotherapy treatment planning tasks:

configuring a variable base layer among the multiple base layers of the base deep learning engine, and generating one of multiple target layers of the target deep learning engine by modifying the variable base layer; and configuring an invariable base layer among the multiple base layers of the base deep learning engine, and generating one of multiple target layers of the target deep learning engine based on feature data generated using the invariable base layer;

performing, by the computer system, the target radiotherapy treatment planning task to generate output data based on input data associated with a particular patient in a third phase using the target deep learning engine, wherein the third phase is later than the second phase; and generating, by the computer system, a treatment plan based on the output data, wherein the treatment delivery system retrieves the treatment plan and delivers a radiotherapy treatment to the particular patient according to the treatment plan.

9. The non-transitory computer-readable storage medium of claim 8, wherein generating the target deep learning engine comprises:

based on the base deep learning engine that is pre-trained to perform the base radiotherapy treatment planning task associated with a base anatomical site, generating the target deep learning engine to perform the target radiotherapy treatment planning task associated with a target anatomical site.

10. The non-transitory computer-readable storage medium of claim 8, wherein generating the target deep learning engine comprises:

based on the base deep learning engine that is pre-trained to perform the base radiotherapy treatment planning task according to a base rule, generating the target deep learning engine to perform the target radiotherapy treatment planning task associated with a target rule.

11. The non-transitory computer-readable storage medium of claim 8, wherein generating the target deep learning engine comprises:

generating the target deep learning engine to perform one of the following target radiotherapy treatment planning tasks: automatic segmentation to generate structure data based on image data; dose prediction to generate dose data based on structure data and image data; and treatment delivery data prediction to generate treatment delivery data.

12. The non-transitory computer-readable storage medium of claim 8, wherein generating the target deep learning engine comprises one of the following:

configuring the multiple base layers of the base deep learning engine to be variable base layers; and generating the multiple target layers by modifying the respective variable base layers based on the target training data.

13. The non-transitory computer-readable storage medium of claim 8, wherein generating the target deep learning engine comprises:

configuring the multiple base layers of the base deep learning engine to be invariable base layers; and generating the feature data using the invariable base layers based on the target training data.

14. The non-transitory computer-readable storage medium of claim 8, wherein generating the target deep learning engine comprises:

configuring the multiple base layers of the base deep learning engine to include both invariable base layers and variable base layers.

15. A computer system interfaced with a treatment delivery system and configured to perform deep transfer learning for radiotherapy treatment planning, wherein the computer system comprises: a processor and a non-transitory computer-readable medium having stored thereon instructions that, when executed by the processor, cause the processor to:

obtain, by the computer system, a base deep learning engine that is pre-trained to perform a base radiotherapy treatment planning task, wherein the base deep learning engine includes multiple base layers; and based on the base deep learning engine, generate, by the computer system, a target deep learning engine to perform a target radiotherapy treatment planning task by performing at least one of the following, wherein the base deep learning engine is trained based on base training data associated with the base radiotherapy treatment planning task in a first phase, the target deep learning engine is trained based on target training data associated with the target radiotherapy treatment planning task in a second phase later than the first phase, and the target radiotherapy treatment planning task and the base radiotherapy treatment planning task are two different radiotherapy treatment planning tasks:

configure a variable base layer among the multiple base layers of the base deep learning engine, and generating one of multiple target layers of the target deep learning engine by modifying the variable base layer; and configure an invariable base layer among the multiple base layers of the base deep learning engine, and generating one of multiple target layers of the target deep learning engine based on feature data generated using the invariable base layer;

perform, by the computer system, the target radiotherapy treatment planning task to generate output data based on input data associated with a particular patient in a third phase using the target deep learning engine, wherein the third phase is later than the second phase; and generate, by the computer system, a treatment plan based on the output data, wherein the treatment delivery system retrieves the treatment plan and delivers a radiotherapy treatment to the particular patient according to the treatment plan.

16. The computer system of claim 15, wherein the instructions for generating the target deep learning engine cause the processor to:

based on the base deep learning engine that is pre-trained to perform the base radiotherapy treatment planning task associated with a base anatomical site, generate the target deep learning engine to perform the target radiotherapy treatment planning task associated with a target anatomical site.

17. The computer system of claim 15, wherein the instructions for generating the target deep learning engine cause the processor to:

based on the base deep learning engine that is pre-trained to perform the base radiotherapy treatment planning task according to a base rule, generate the target deep learning engine to perform the target radiotherapy treatment planning task associated with a target rule.

18. The computer system of claim 15, wherein the instructions for generating the target deep learning engine cause the processor to:

generate the target deep learning engine to perform one of the following target radiotherapy treatment planning tasks: automatic segmentation to generate structure data based on image data; dose prediction to generate dose data based on structure data and image data; and treatment delivery data prediction to generate treatment delivery data.

19. The computer system of claim 15, wherein the instructions for generating the target deep learning engine cause the processor to:

configure the multiple base layers of the base deep learning engine to be variable base layers; and generate the multiple target layers by modifying the respective variable base layers based on the target training data.

20. The computer system of claim 15, wherein the instructions for generating the target deep learning engine cause the processor to:

configure the multiple base layers of the base deep learning engine to be invariable base layers; and generate the feature data using the invariable base layers based on the target training data.

21. The computer system of claim 15, wherein the instructions for generating the target deep learning engine cause the processor to:

configure the multiple base layers of the base deep learning engine to include both invariable base layers and variable base layers.

22. The method of claim 1, wherein the treatment plan includes data to control the treatment delivery system.

* * * * *